United States Patent
Sicvol et al.

(10) Patent No.: US 7,854,751 B2
(45) Date of Patent: *Dec. 21, 2010

(54) PERCUTANEOUS ACCESS DEVICES AND BONE ANCHOR ASSEMBLIES

(75) Inventors: Christopher Sicvol, Boston, MA (US); Erasmo Lopez, Seattle, WA (US); Ramon Ruberte, Ann Arbor, MI (US)

(73) Assignee: Dupuy Spine, Inc., Raynham, MA (US)

( * ) Notice: Subject to any disclaimer, the term of this patent is extended or adjusted under 35 U.S.C. 154(b) by 82 days.

This patent is subject to a terminal disclaimer.

(21) Appl. No.: 11/692,531

(22) Filed: Mar. 28, 2007

(65) Prior Publication Data

US 2007/0167954 A1   Jul. 19, 2007

Related U.S. Application Data

(63) Continuation of application No. 11/672,539, filed on Feb. 8, 2007, now abandoned, which is a continuation of application No. 10/738,286, filed on Dec. 16, 2003, now Pat. No. 7,179,261.

(51) Int. Cl.
 *A61B 17/70* (2006.01)
(52) U.S. Cl. .................... 606/246; 606/86 A
(58) Field of Classification Search ............ 606/96, 606/99, 104, 323, 86 A, 916, 246, 251, 252, 606/273–274, 276
See application file for complete search history.

(56) References Cited

U.S. PATENT DOCUMENTS

| | | | |
|---|---|---|---|
| 2,005,955 A | 6/1935 | Knox | |
| 2,248,054 A | 7/1941 | Becker | |
| 2,268,576 A | 1/1942 | Drewett | |
| 2,346,346 A | 4/1944 | Anderson | |
| 2,514,589 A | 7/1950 | Penman | |
| 2,684,168 A | 7/1954 | McGinnis et al. | |

(Continued)

FOREIGN PATENT DOCUMENTS

DE   26 49 042 B1   1/1978

(Continued)

OTHER PUBLICATIONS

"CD Horizon Legacy 5.5 Spinal System" Brochure, Medtronic Sofamor Danek, USA Inc., 2003.

(Continued)

*Primary Examiner*—Thomas C Barrett
*Assistant Examiner*—Nicholas Woodall

(57) ABSTRACT

A percutaneous access device includes an inner tube and an outer tube disposed about at least a portion of the inner tube. The outer tube may be sized to span from a skin incision in a patient to a site proximate the spine of the patient. The distal end of the outer tube may be adapted to releasably engage a bone anchor. The inner tube may be adjustable relative to the outer tube between a first position and a second position in which the distal end of the inner tube contacts the bone anchor. A bone anchor assembly includes a bone anchor having a distal bone engaging portion and a receiving member having a recess for receiving a spinal fixation element. The proximal end of the receiving member may have an arcuate groove formed on an exterior surface thereof to facilitate connection of an instrument to the receiving member.

8 Claims, 26 Drawing Sheets

U.S. PATENT DOCUMENTS

| | | |
|---|---|---|
| 3,224,799 A | 12/1965 | Blose et al. |
| 3,997,138 A | 12/1976 | Crock et al. |
| 4,041,636 A | 8/1977 | Folker |
| 4,274,401 A | 6/1981 | Miskew |
| 4,324,036 A | 4/1982 | Reilly |
| 4,369,011 A | 1/1983 | Ploss |
| 4,373,754 A | 2/1983 | Bollfrass et al. |
| 4,382,438 A | 5/1983 | Jacobs |
| 4,492,749 A | 1/1985 | Scheler |
| 4,611,580 A | 9/1986 | Wu |
| 4,763,644 A | 8/1988 | Webb |
| 4,799,372 A | 1/1989 | Marcon et al. |
| 4,815,453 A | 3/1989 | Cotrel |
| 4,836,196 A | 6/1989 | Park et al. |
| 4,848,368 A | 7/1989 | Kronner |
| 4,851,453 A | 7/1989 | White et al. |
| 4,864,614 A | 9/1989 | Crowther |
| 4,887,596 A | 12/1989 | Sherman |
| 4,913,134 A | 4/1990 | Luque |
| 4,946,458 A | 8/1990 | Harms et al. |
| 4,950,269 A | 8/1990 | Gaines, Jr. |
| 5,005,562 A | 4/1991 | Cotrel |
| 5,042,982 A | 8/1991 | Harms et al. |
| 5,052,643 A | 10/1991 | Law |
| 5,067,955 A | 11/1991 | Cotrel |
| 5,092,635 A | 3/1992 | DeLange et al. |
| 5,092,867 A | 3/1992 | Harms et al. |
| 5,092,893 A | 3/1992 | Smith |
| 5,129,388 A | 7/1992 | Vignaud et al. |
| 5,154,719 A | 10/1992 | Cotrel |
| 5,171,279 A | 12/1992 | Mathews |
| 5,176,680 A | 1/1993 | Vignaud et al. |
| 5,196,013 A | 3/1993 | Harms et al. |
| 5,207,678 A | 5/1993 | Harms et al. |
| 5,217,497 A | 6/1993 | Mehdian |
| 5,242,446 A | 9/1993 | Steffee et al. |
| 5,261,907 A | 11/1993 | Vignaud et al. |
| 5,261,912 A | 11/1993 | Frigg |
| 5,261,913 A | 11/1993 | Marnay |
| 5,282,862 A | 2/1994 | Baker et al. |
| 5,282,863 A | 2/1994 | Burton |
| 5,352,231 A | 10/1994 | Brumfield et al. |
| 5,360,431 A | 11/1994 | Puno et al. |
| 5,385,583 A | 1/1995 | Cotrel |
| 5,397,363 A | 3/1995 | Gelbard |
| 5,429,639 A | 7/1995 | Judet |
| 5,443,467 A | 8/1995 | Biedermann et al. |
| 5,466,237 A | 11/1995 | Byrd, III et al. |
| 5,468,241 A | 11/1995 | Metz-Stavenhagen et al. |
| 5,474,555 A | 12/1995 | Puno et al. |
| 5,496,321 A | 3/1996 | Puno et al. |
| 5,520,689 A | 5/1996 | Schlapfer et al. |
| 5,536,268 A | 7/1996 | Griss |
| 5,545,165 A | 8/1996 | Biedermann et al. |
| 5,554,157 A | 9/1996 | Errrico et al. |
| 5,569,248 A | 10/1996 | Mathews |
| 5,584,887 A | 12/1996 | Kambin |
| 5,586,984 A | 12/1996 | Errico et al. |
| 5,605,457 A | 2/1997 | Bailey et al. |
| 5,647,873 A | 7/1997 | Errico et al. |
| 5,651,789 A | 7/1997 | Cotrel |
| 5,667,508 A | 9/1997 | Errico et al. |
| 5,669,911 A | 9/1997 | Errico et al. |
| 5,672,176 A | 9/1997 | Biedermann et al. |
| 5,680,963 A | 10/1997 | Brusko |
| 5,683,390 A | 11/1997 | Metz-Stavenhagen et al. |
| 5,683,391 A | 11/1997 | Boyd |
| 5,690,630 A | 11/1997 | Errico et al. |
| 5,716,356 A | 2/1998 | Biedermann et al. |
| 5,725,527 A | 3/1998 | Biedermann et al. |
| 5,733,286 A | 3/1998 | Errico et al. |
| 5,738,685 A | 4/1998 | Halm et al. |
| 5,782,833 A | 7/1998 | Haider |
| 5,788,697 A | 8/1998 | McInnes |
| 5,797,911 A | 8/1998 | Sherman et al. |
| 5,810,818 A | 9/1998 | Errico |
| 5,817,094 A | 10/1998 | Errico et al. |
| 5,858,020 A | 1/1999 | Johnson et al. |
| 5,863,293 A | 1/1999 | Richelsoph |
| 5,873,878 A | 2/1999 | Harms et al. |
| 5,879,350 A | 3/1999 | Shermann et al. |
| 5,882,350 A | 3/1999 | Ralph et al. |
| 5,885,286 A | 3/1999 | Sherman et al. |
| 5,888,221 A | 3/1999 | Gelbard |
| 5,891,145 A | 4/1999 | Morrison et al. |
| 5,899,901 A | 5/1999 | Middleton |
| 5,899,904 A | 5/1999 | Errico |
| 5,899,905 A | 5/1999 | Errico et al. |
| 5,925,047 A | 7/1999 | Errico et al. |
| 5,947,969 A | 9/1999 | Errico et al. |
| 5,961,266 A | 10/1999 | Tsenge |
| 5,964,760 A | 10/1999 | Richelsoph |
| 5,976,146 A | 11/1999 | Ogawa |
| 5,984,922 A | 11/1999 | McKay |
| 5,984,923 A | 11/1999 | Breard |
| 5,989,254 A | 11/1999 | Katz |
| 6,004,349 A | 12/1999 | Jackson |
| 6,010,503 A | 1/2000 | Richelsoph |
| 6,033,406 A | 3/2000 | Mathews |
| 6,053,917 A | 4/2000 | Sherman et al. |
| 6,056,753 A | 5/2000 | Jackson |
| 6,059,786 A | 5/2000 | Jackson |
| 6,074,391 A | 6/2000 | Metz-Stavenhagen et al. |
| 6,077,262 A | 6/2000 | Schlapfer et al. |
| 6,083,225 A | 7/2000 | Winslow et al. |
| 6,083,227 A | 7/2000 | Saurat et al. |
| 6,090,110 A | 7/2000 | Metz-Stravenhagen |
| 6,090,111 A | 7/2000 | Nichols |
| 6,099,528 A | 8/2000 | Saurat |
| 6,102,912 A | 8/2000 | Cazin et al. |
| 6,102,913 A | 8/2000 | Jackson |
| 6,113,602 A | 9/2000 | Sand |
| 6,120,760 A | 9/2000 | Hotten et al. |
| 6,132,431 A | 10/2000 | Nilsson et al. |
| 6,132,432 A | 10/2000 | Richelsoph |
| 6,139,549 A * | 10/2000 | Keller ..................... 606/86 A |
| 6,139,551 A | 10/2000 | Michelson et al. |
| 6,183,472 B1 | 2/2001 | Lutz |
| RE37,161 E | 5/2001 | Michelson et al. |
| 6,224,598 B1 | 5/2001 | Jackson |
| 6,235,028 B1 | 5/2001 | Brumfield et al. |
| 6,251,112 B1 | 6/2001 | Jackson |
| 6,254,602 B1 | 7/2001 | Justis |
| 6,258,090 B1 | 7/2001 | Jackson |
| 6,261,287 B1 | 7/2001 | Metz-Stavenhagen |
| 6,280,442 B1 | 8/2001 | Barker et al. |
| 6,296,642 B1 | 10/2001 | Morrison et al. |
| 6,299,616 B1 | 10/2001 | Beger |
| 6,302,633 B1 | 10/2001 | Poe |
| 6,315,564 B1 | 11/2001 | Levisman |
| 6,331,179 B1 | 12/2001 | Freid et al. |
| 6,355,040 B1 | 3/2002 | Richelsoph et al. |
| 6,358,254 B1 | 3/2002 | Anderson |
| 6,361,535 B2 | 3/2002 | Jackson |
| 6,368,321 B1 | 4/2002 | Jackson |
| 6,371,989 B1 | 4/2002 | Chauvin et al. |
| 6,379,356 B1 | 4/2002 | Jackson |
| 6,387,097 B1 | 5/2002 | Alby |
| 6,416,515 B1 | 7/2002 | Wagner |
| 6,428,541 B1 | 8/2002 | Boyd |
| 6,440,132 B1 | 8/2002 | Jackson |
| 6,440,133 B1 | 8/2002 | Beale et al. |
| 6,440,137 B1 | 8/2002 | Horvath et al. |
| 6,443,953 B1 | 9/2002 | Perra et al. |

| | | |
|---|---|---|
| 6,454,768 B1 | 9/2002 | Jackson |
| 6,454,772 B1 | 9/2002 | Jackson |
| 6,458,131 B1 | 10/2002 | Ray |
| 6,458,132 B2 | 10/2002 | Choi |
| 6,468,276 B1 | 10/2002 | McKay |
| 6,471,705 B1 | 10/2002 | Biedermann et al. |
| 6,475,218 B2 | 11/2002 | Gournay et al. |
| 6,485,220 B2 | 11/2002 | Hecht |
| 6,485,491 B1 | 11/2002 | Farris et al. |
| 6,485,518 B1 | 11/2002 | Cornwall et al. |
| 6,487,798 B2 | 12/2002 | Seushige |
| 6,488,681 B2 | 12/2002 | Martin et al. |
| 6,488,682 B2 | 12/2002 | Kikuchi et al. |
| 6,488,683 B2 | 12/2002 | Lieberman |
| 6,520,990 B1 | 2/2003 | Ray |
| 6,524,315 B1 | 2/2003 | Selvitelli et al. |
| 6,530,028 B1 | 3/2003 | Yokoyama |
| 6,530,929 B1 * | 3/2003 | Justis et al. ................ 606/103 |
| 6,537,276 B2 | 3/2003 | Metz-Stavenhagen |
| 6,540,748 B2 | 4/2003 | Lombardo |
| 6,540,749 B2 | 4/2003 | Schafer et al. |
| 6,554,831 B1 | 4/2003 | Rivard |
| 6,554,834 B1 | 4/2003 | Crozet |
| 6,641,586 B2 | 11/2003 | Varieur |
| 6,648,888 B1 | 11/2003 | Shluzas |
| 6,652,527 B2 | 11/2003 | Zucherman |
| 6,723,100 B2 | 4/2004 | Biederamann et al. |
| 6,726,689 B2 | 4/2004 | Jackson |
| 6,730,089 B2 | 5/2004 | Jackson |
| 6,755,829 B1 | 6/2004 | Bono |
| 6,793,656 B1 | 9/2004 | Mathews |
| 6,837,889 B2 | 1/2005 | Shluzas |
| 6,905,500 B2 | 6/2005 | Jeon |
| 6,911,030 B1 | 6/2005 | Vanacker et al. |
| 7,081,117 B2 | 7/2006 | Bono |
| 7,125,426 B2 | 10/2006 | Moumene |
| 7,156,850 B2 | 1/2007 | Kim |
| 7,179,261 B2 | 2/2007 | Sicvol |
| 7,250,052 B2 * | 7/2007 | Landry et al. ............. 606/86 A |
| 7,527,638 B2 | 5/2009 | Anderson |
| 7,666,188 B2 | 2/2010 | Anderson |
| 2001/0001119 A1 | 5/2001 | Lombardo |
| 2001/0010000 A1 | 7/2001 | Gertzben |
| 2001/0023350 A1 | 9/2001 | Choi |
| 2001/0025180 A1 | 9/2001 | Jackson |
| 2001/0034521 A1 | 10/2001 | Bailey |
| 2002/0007183 A1 | 1/2002 | Lee |
| 2002/0010467 A1 | 1/2002 | Cooper |
| 2002/0013585 A1 | 1/2002 | Gournay et al. |
| 2002/0022842 A1 | 2/2002 | Horvath et al. |
| 2002/0026192 A1 | 2/2002 | Schmiel |
| 2002/0026193 A1 | 2/2002 | Barker et al. |
| 2002/0032443 A1 | 3/2002 | Sherman |
| 2002/0035366 A1 | 3/2002 | Walden |
| 2002/0040243 A1 | 4/2002 | Attali |
| 2002/0045898 A1 | 4/2002 | Freid |
| 2002/0049444 A1 | 4/2002 | Knox |
| 2002/0055739 A1 | 5/2002 | Lieberman |
| 2002/0058942 A1 | 5/2002 | Biedermann et al. |
| 2002/0068938 A1 | 6/2002 | Jackson |
| 2002/0068940 A1 | 6/2002 | Gaines |
| 2002/0082602 A1 | 6/2002 | Biedermann |
| 2002/0091386 A1 | 7/2002 | Martin |
| 2002/0095153 A1 | 7/2002 | Jones et al. |
| 2002/0111626 A1 | 8/2002 | Ralph et al. |
| 2002/0111628 A1 | 8/2002 | Ralph et al. |
| 2002/0116000 A1 | 8/2002 | Zucherman et al. |
| 2002/0116001 A1 | 8/2002 | Schafer |
| 2002/0120272 A1 | 8/2002 | Yuan et al. |
| 2002/0133154 A1 | 9/2002 | Saint Martin |
| 2002/0138076 A1 | 9/2002 | Biedermann et al. |
| 2002/0138077 A1 | 9/2002 | Ferree |
| 2002/0143341 A1 | 10/2002 | Biedermann et al. |
| 2002/0161368 A1 | 10/2002 | Foley et al. |
| 2002/0169448 A1 | 11/2002 | Vanacker |
| 2002/0169450 A1 | 11/2002 | Lange |
| 2002/0173791 A1 | 11/2002 | Howland |
| 2002/0183747 A1 | 12/2002 | Jao et al. |
| 2002/0183748 A1 | 12/2002 | Martin et al. |
| 2002/0183749 A1 | 12/2002 | Burgess et al. |
| 2002/0188295 A1 | 12/2002 | Martz |
| 2003/0004511 A1 | 1/2003 | Ferree |
| 2003/0004512 A1 | 1/2003 | Farris et al. |
| 2003/0009168 A1 | 1/2003 | Beale et al. |
| 2003/0023240 A1 | 1/2003 | Amrein et al. |
| 2003/0023243 A1 | 1/2003 | Biedermann et al. |
| 2003/0028190 A1 | 2/2003 | Patel |
| 2003/0032957 A1 | 2/2003 | McKinley |
| 2003/0045875 A1 | 3/2003 | Bertranov |
| 2003/0045879 A1 | 3/2003 | Minfelde et al. |
| 2003/0050640 A1 | 3/2003 | Lee et al. |
| 2003/0055426 A1 | 3/2003 | Carbone et al. |
| 2003/0055427 A1 | 3/2003 | Graf |
| 2003/0060823 A1 | 3/2003 | Bryan |
| 2003/0060824 A1 | 3/2003 | Viart |
| 2003/0060826 A1 | 3/2003 | Foley |
| 2003/0083657 A1 | 5/2003 | Drewry |
| 2003/0100896 A1 | 5/2003 | Biedermann et al. |
| 2003/0100904 A1 | 5/2003 | Biedermann |
| 2003/0208203 A1 | 11/2003 | Lim et al. |
| 2003/0216748 A1 | 11/2003 | Gitis |
| 2003/0216768 A1 | 11/2003 | Gitis |
| 2003/0229347 A1 | 12/2003 | Sherman |
| 2004/0039384 A1 | 2/2004 | Boehm et al. |
| 2004/0138662 A1 | 7/2004 | Landry |
| 2004/0143265 A1 | 7/2004 | Landry |
| 2004/0181224 A1 | 9/2004 | Biedermann |
| 2004/0204711 A1 | 10/2004 | Jackson |
| 2004/0243139 A1 | 12/2004 | Lewis |
| 2005/0010221 A1 | 1/2005 | Dalton |
| 2005/0038432 A1 | 2/2005 | Shaolian |
| 2005/0065517 A1 | 3/2005 | Chin |
| 2005/0085813 A1 | 4/2005 | Spitler |
| 2005/0113832 A1 | 5/2005 | Molz et al. |
| 2005/0171540 A1 | 8/2005 | Lim et al. |
| 2005/0171549 A1 | 8/2005 | Boehm et al. |
| 2005/0192570 A1 | 9/2005 | Jackson |
| 2005/0192571 A1 | 9/2005 | Abdelgany |
| 2007/0129731 A1 | 6/2007 | Sicvol |

FOREIGN PATENT DOCUMENTS

| | | |
|---|---|---|
| DE | 29 03 342 A1 | 7/1980 |
| DE | 3434807 A1 | 12/1985 |
| DE | 3639810 A1 | 5/1988 |
| DE | 3711013 C1 | 6/1988 |
| DE | 8915443.6 | 7/1990 |
| DE | 9006568.9 | 12/1990 |
| DE | 3916198 C2 | 7/1992 |
| DE | 430 7576 | 4/1994 |
| DE | 9403231.9 | 6/1994 |
| DE | 298 10 798 U1 | 12/1999 |
| DE | 199 12 364 A1 | 10/2000 |
| DE | 100 27 988 A1 | 1/2002 |
| DE | 101 36 129 A1 | 2/2003 |
| DE | 101 57 969 C1 | 2/2003 |
| DE | 199 12 364 B4 | 10/2004 |
| EP | 0242708 A2 | 4/1987 |
| EP | 0283373 A1 | 3/1988 |
| EP | 0346521 | 7/1988 |
| EP | 0328883 A2 | 1/1989 |
| EP | 0330881 A1 | 2/1989 |
| EP | 0348272 | 6/1989 |
| EP | 0379551 | 7/1989 |
| EP | 0392927 | 4/1990 |
| EP | 0452451 | 11/1990 |

| | | |
|---|---|---|
| EP | 0441729 | 2/1991 |
| EP | 0465158 | 6/1991 |
| EP | 0528706 | 7/1992 |
| EP | 0572790 | 4/1993 |
| EP | 0324022 | 9/1993 |
| EP | 0614649 | 2/1994 |
| EP | 0771635 | 10/1996 |
| EP | 0836835 A2 | 10/1996 |
| EP | 0870474 | 7/1997 |
| EP | 1332722 | 5/1998 |
| EP | 1090595 A2 | 4/2001 |
| EP | 1133951 A2 | 3/2002 |
| EP | 1190678 A2 | 3/2002 |
| EP | 1332722 A1 | 8/2003 |
| FR | 2 624 720 | 12/1987 |
| FR | 2 659 546 | 3/1990 |
| GB | 522747 | 6/1940 |
| JP | 64 76847 | 3/1989 |
| WO | WO 89 00028 A1 | 1/1989 |
| WO | WO 90 00377 A1 | 1/1990 |
| WO | WO 91 06254 A1 | 5/1991 |
| WO | WO 91 16020 A1 | 10/1991 |
| WO | WO 92 20294 A1 | 11/1992 |
| WO | WO 93 11715 A1 | 6/1993 |
| WO | WO 94 14384 A2 | 7/1994 |
| WO | WO 95 01132 A1 | 1/1995 |
| WO | WO 95 13755 A1 | 5/1995 |
| WO | WO 95 13756 A1 | 5/1995 |
| WO | WO 95 14437 A1 | 6/1995 |
| WO | WO 98 12977 A1 | 4/1998 |
| WO | WO 00 27297 A1 | 5/2000 |
| WO | WO 01 01873 A1 | 1/2001 |
| WO | WO 02069854 | 9/2002 |
| WO | WO 2004 041100 A1 | 5/2004 |
| WO | WO 2005 041799 A1 | 5/2005 |
| WO | WO 2005041799 | 5/2005 |

OTHER PUBLICATIONS

John R. Walker, "Machining Fundamentals Fundamental Basic to Industry", The Goodheart-Wilcox Co., Inc., 1981, pp. 2,179-2,186, including redacted version.

Lascoe et al., "Machineshop—Operations and Setups", American Technical Society, 1973, pp. 380, 386 and 388 including redacted version.

Jeanneret, Posterior Rod System of the Cervical Spine: A New Implant Allowing Optimal Screw Insertion, Eur. Spine J 1996; pp. 350-356, 5(5):Springer-Verlag.

Kaneda et al; New Anterior Instrumentation For the Management of Thoracolumbar and Lumbar Scoliosis; Spine May 15, 1996; pp. 1250-1261; vol. 21(10).

Glazer et al.; Biomechanical analysis of Multilevel Fixation Methods in the Lumbar Spine; Spine Jan. 15, 1997; pp. 171-182;vol. 22(2).

Shapiro et al.; Spinal Instrumentation With a Low Complication Rate; Surg. Neurol. Dec. 1997; pp. 566-574; vol. 48(6) Elsevier Science.

Viau et al.; Thoracic Pedicle Screw Instrumentation Using the "Funnell Technique"; J. Spinal Discord Tech. Dec. 2002; pp. 450-453; vol. 15(6).

*U&I Corporation Thoracolumbar Spine Optima Spinal System from website* www.uandi.co.kr pp. 1-2 Nov. 10, 2005.

Ltr to Robert Malone from Dept of Health & Human Services, Jun. 20, 2002 regarding Forex Corporation OPTIMA™ Devices 510(k) Summary, 5 pages.

Ebara et al; A New System For the Anterio Restoration and Fixation of Thoracic Spinal Deformities Using an Andoscopic Approach; Spine Apr. 1, 2000;pp. 876-883; vol. 25(7).

XIA Spinal System Brochure, Stryker Howmedica Osteonics, pp. 1-7, Stryker Corporation, Rutherford, NJ. Jul. 1999.

OPTIMA Spinal System Surgical Technique Brochure, pp. 1-17, 2005.

* cited by examiner

PERCUTANEOUS ACCESS DEVICES AND BONE ANCHOR ASSEMBLIES

CROSS-REFERENCE TO RELATED APPLICATIONS

This application is a continuation of U.S. patent application Ser. No. 11/672,539, filed Feb. 8, 2007, now abandoned, which is a continuation of U.S. patent application Ser. No. 10/738,286, filed Dec. 16, 2003, now U.S Pat. No. 7,179,261. Each of the previously mentioned patent application is incorporated herein by reference.

BACKGROUND

For a number of known reasons, spinal fixation devices are used in orthopedic surgery to align and/or fix a desired relationship between adjacent vertebral bodies. Such devices typically include a spinal fixation element, such as a relatively rigid fixation rod or plate, that is coupled to adjacent vertebrae by attaching the element to various anchoring devices, such as hooks, bolts, wires, or screws. The fixation elements can have a predetermined contour that has been designed according to the properties of the target implantation site, and once installed, the fixation element holds the vertebrae in a desired spatial relationship, either until desired healing or spinal fusion has taken place, or for some longer period of time.

Spinal fixation elements can be anchored to specific portions of the vertebrae. Since each vertebra varies in shape and size, a variety of anchoring devices have been developed to facilitate engagement of a particular portion of the bone. Pedicle screw assemblies, for example, have a shape and size that is configured to engage pedicle bone. Such screws typically include a threaded shank that is adapted to be threaded into a vertebra, and a head portion having a rod-receiving element, usually in the form of a U-shaped recess formed in the head. A set-screw, plug, or similar type of closure mechanism is used to lock the fixation element, e.g., a spinal rod, into the rod-receiving head of the pedicle screw. In use, the shank portion of each screw is threaded into a vertebra, and once properly positioned, a rod is seated through the rod-receiving member of each screw and the rod is locked in place by tightening a cap or other closure mechanism to securely interconnect each screw and the fixation rod.

Recently, the trend in spinal surgery has been moving toward providing minimally invasive devices and methods for implanting bone anchors and spinal fixation devices.

SUMMARY

Disclosed herein are percutaneous access devices that facilitate the delivery and implanting of bone anchors into bone, in particular, one or more vertebral bodies of the spine. In particular, the disclosed percutaneous access devices permit the delivery and implanting of one or more bone anchors in a minimally invasive manner thereby limiting trauma to surrounding tissue. Moreover, the percutaneous access devices disclosed herein can provide a percutaneous pathway between a skin incision and the bone anchor that may be used to deliver components of the bone anchor, such as the fastening mechanism, the fixation element, and/or instruments to the bone anchor. Also, disclosed herein are bone anchors that facilitate the connection of instruments, such as a percutaneous access device, to the bone anchor.

In accordance with one exemplary embodiment, a percutaneous access device includes an inner tube and an outer tube disposed about at least a portion of the inner tube. The outer tube, in the exemplary embodiment, is sized to span from at least a skin incision in a patient to a predetermined site proximate the spine of the patient. The distal end of the outer tube may be adapted to releasably engage a bone anchor. The inner tube, in the exemplary embodiment, may be adjustable relative to the outer tube along the longitudinal axis of the outer tube between a first position and a second position in which the distal end of the inner tube contacts the bone anchor.

In accordance with another exemplary embodiment, a bone anchor assembly includes a bone anchor having a proximal head and a distal bone engaging portion and a receiving member coupled to the bone anchor. The receiving member, in the exemplary embodiment, may have a proximal end, a distal end and a recess for receiving a spinal fixation element, such as a rod or a plate. The proximal end of the receiving member, in the exemplary embodiment, may have at least one arcuate groove formed on an exterior surface thereof to facilitate connection of an instrument, such as a percutaneous access device, to the receiving member.

BRIEF DESCRIPTION OF THE DRAWINGS

These and other features and advantages of the percutaneous access devices and bone anchor assemblies disclosed herein will be more fully understood by reference to the following detailed description in conjunction with the attached drawings in which like reference numerals refer to like elements through the different views. The drawings illustrate principles of the percutaneous access devices and bone anchor assemblies disclosed herein and, although not to scale, show relative dimensions.

DETAILED DESCRIPTION

Figure 1:
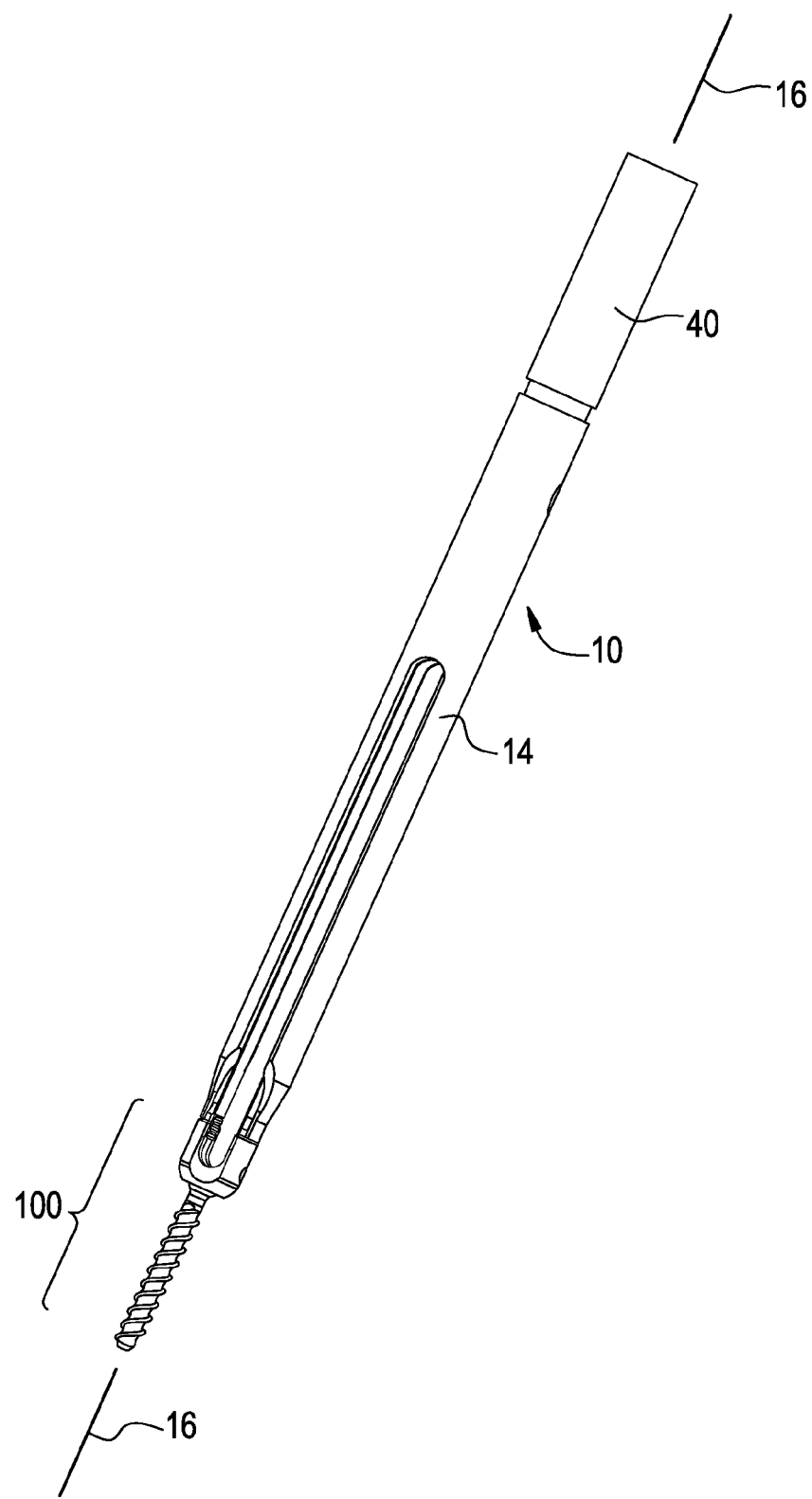
FIG. 1 is a perspective view of an exemplary embodiment of a percutaneous access device.
Figure 2:
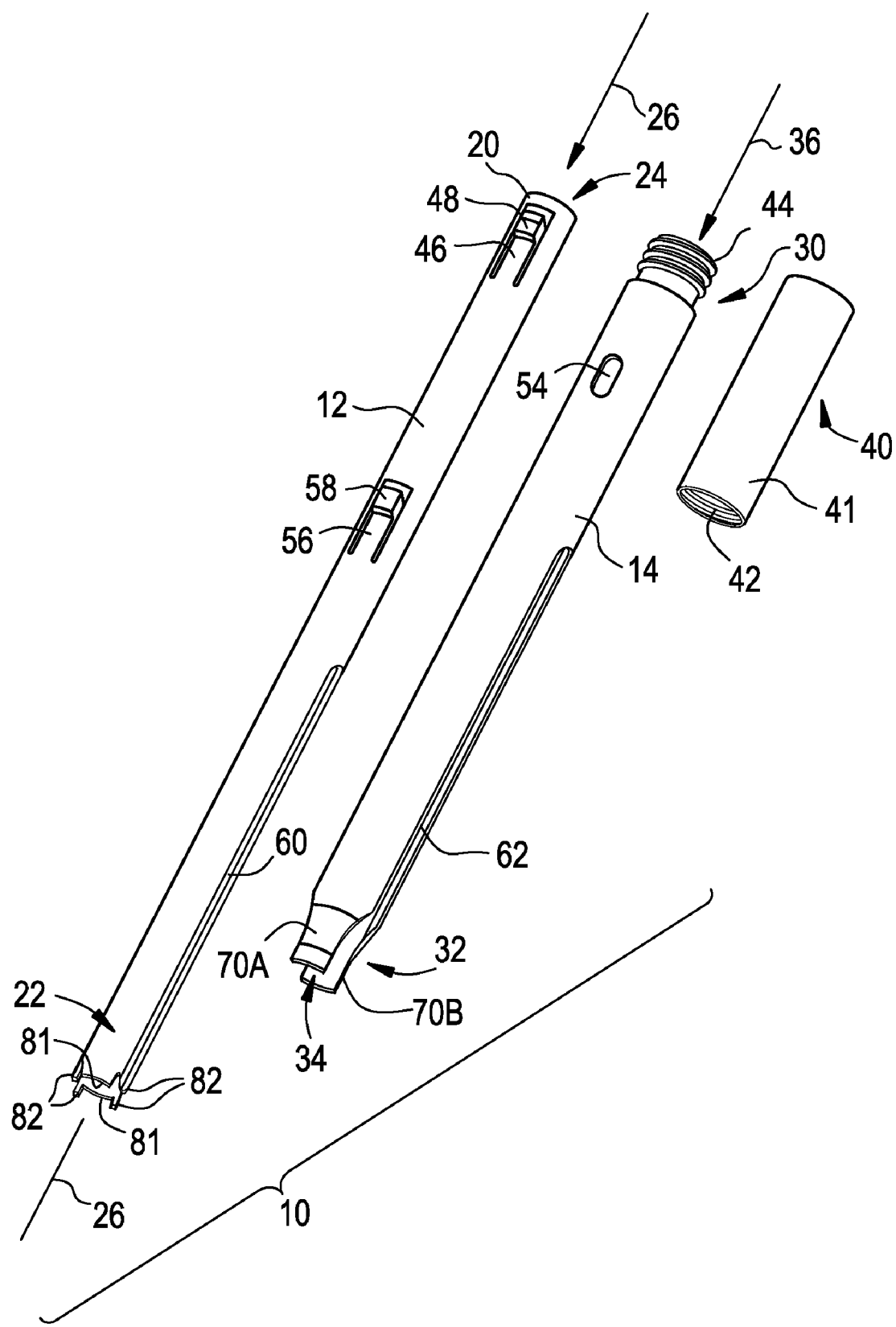
FIG. 2 is a perspective view of the components of the percutaneous access device of FIG. 1.

Certain exemplary embodiments will now be described to provide an overall understanding of the principles of the structure, function, manufacture, and use of the percutaneous access devices and bone anchor assemblies disclosed herein. One or more examples of these embodiments are illustrated in the accompanying drawings. Those of ordinary skill in the art will understand that the percutaneous access devices and bone anchor assemblies specifically described herein and illustrated in the accompanying drawings are non-limiting exemplary embodiments and that the scope of the present invention is defined solely be the claims. The features illustrated or described in connection with one exemplary embodiment may be combined with the features of other embodiments. Such modifications and variations are intended to be included within the scope of the present invention.

The articles "a" and "an" are used herein to refer to one or to more than one (i.e. to at least one) of the grammatical object of the article. By way of example, "an element" means one element or more than one element.

The term "distal" as used herein with respect to any component or structure will generally refer to a position or orientation that is proximate, relatively, to the bone surface to which a bone anchor is to be applied. Conversely, the term "proximal" as used herein with respect to any component or structure will generally refer to a position or orientation that is distant, relatively, to the bone surface to which a bone anchor is to be applied.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

FIGS. 1-5 illustrate an exemplary embodiment of a percutaneous access device 10. The exemplary percutaneous access device 10 can facilitate the delivery and implanting of a bone anchor, such as the exemplary bone anchor assembly 100 illustrated and described below, into bone, in particular, one or more vertebral bodies of the spine. In particular, the exemplary percutaneous access device 10 can facilitate the delivery and implanting of a bone anchor in a minimally invasive manner and can provide a percutaneous pathway between a skin incision in the patent and the bone anchor that may be used to deliver components of the bone anchor, such as the closure mechanism, one or more fixation elements, and/or instruments to the bone anchor. The percutaneous access device 10 is preferably adapted to be introduced through a minimally invasive percutaneous incision, which is a relatively small incision that typically has a length less than the diameter or width of the device being inserted therethrough. Although the exemplary percutaneous access device 10 described below is designed primarily for use in spinal applications, one skilled in the art will appreciate that the exemplary percutaneous access device 10, as well as the other exemplary embodiments described below, may be used to facilitate the implantation of any type of bone anchor to any type of bone.

The exemplary percutaneous access device 10 includes an inner tube 12 and an outer tube 14 disposed about at least a portion of the inner tube 12. In the illustrated exemplary embodiment, the outer tube 14 is coaxially disposed about the inner tube 12 such that the inner tube 12 and the outer tube 14 share a common longitudinal axis 16. One skilled in the art will appreciate, however, that the outer tube 14 and inner tube 12 need not be coaxially aligned. The inner tube 12 and the outer tube 14, in the exemplary embodiment, are generally cylindrical in shape, having an approximately circular cross-section. One skilled in the art will appreciate, however, the inner tube 12 and the outer tube 14 may have other cross-sectional shapes, including, for example, elliptical or rectilinear. In the exemplary embodiment, the inner tube 12 and outer tube 14 have analogous cross-sections, however, one skilled in the art will appreciate the inner tube 12 and the outer tube 14 can have different cross-sectional shapes. The axial length of the inner tube 12 and outer tube 12 may vary depending on, for example, the patient anatomy, the procedures employed, and/or, that area of the spine in which the device 10 is employed. The inner tube 12 and the outer tube 14 may be linear, as in the exemplary embodiment, or may be curved or angled along one or more sections or the entire length thereof. The inner tube 12 and the outer tube 14 may be constructed from any suitable biocompatible material, including, for example, a metal, such as stainless steel, or a polymer, from any conventional method of manufacturing medical devices.

Although the illustrated exemplary embodiment includes an inner tube and an outer tube, one skilled in the art will appreciate that any number of tubes, e.g., one or more tubes, may be employed depending on, for example, the type of bone anchor employed and the manner by which the device is releasably engaged to the bone anchor. For example, exemplary embodiments of a percutaneous access device having a single outer tube are described below.

Figure 3:
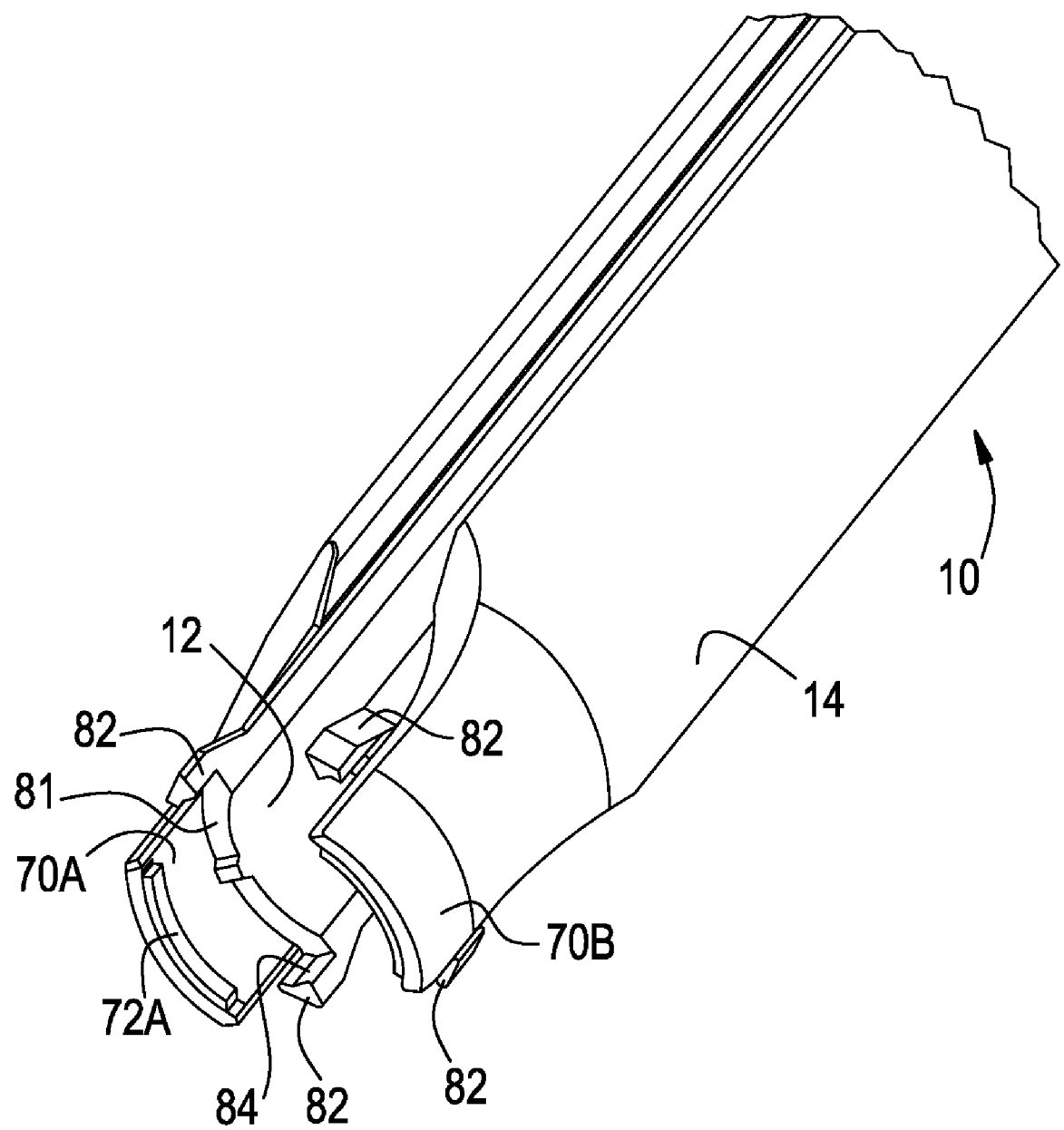
FIG. 3 is a perspective view of the distal end of the percutaneous access device of FIG. 1.
Figure 4:
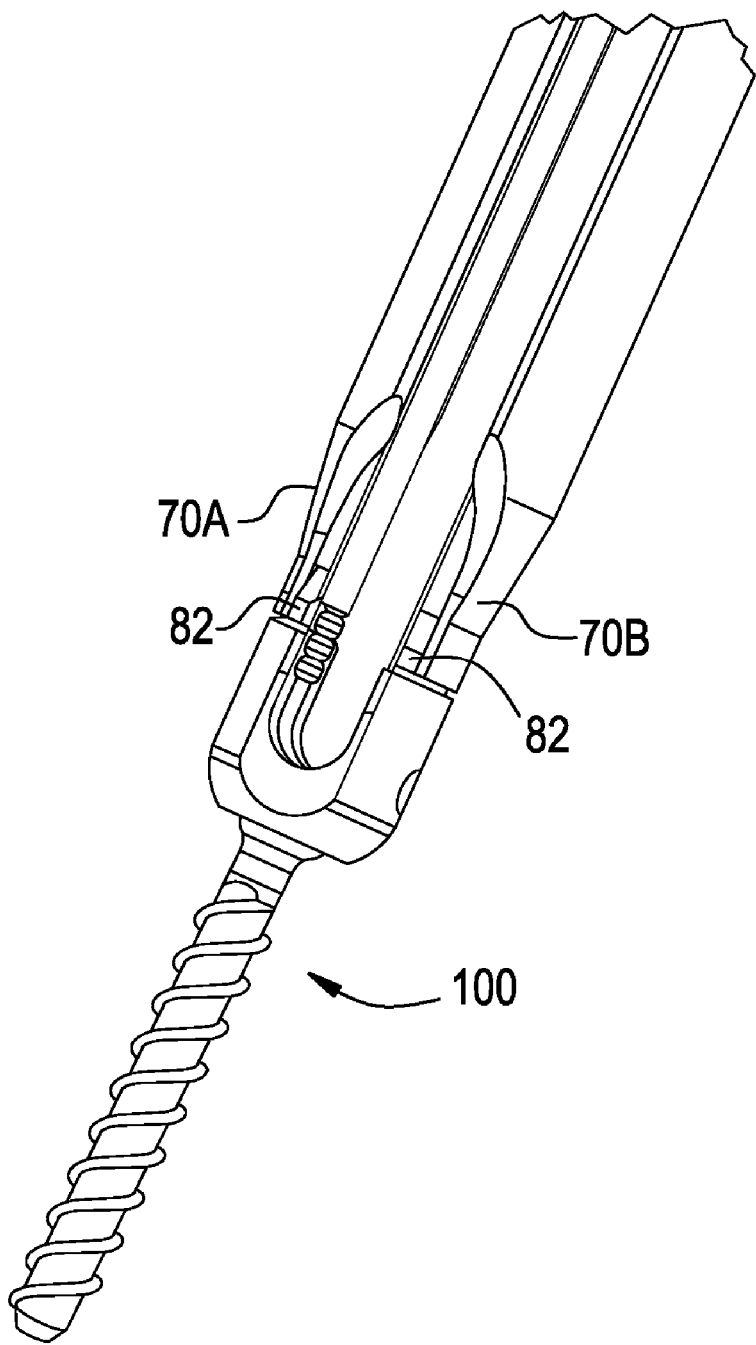
FIG. 4 is a perspective view of the distal end of the percutaneous access device of FIG. 1 coupled to an exemplary embodiment of a bone anchor assembly.
Figure 7:
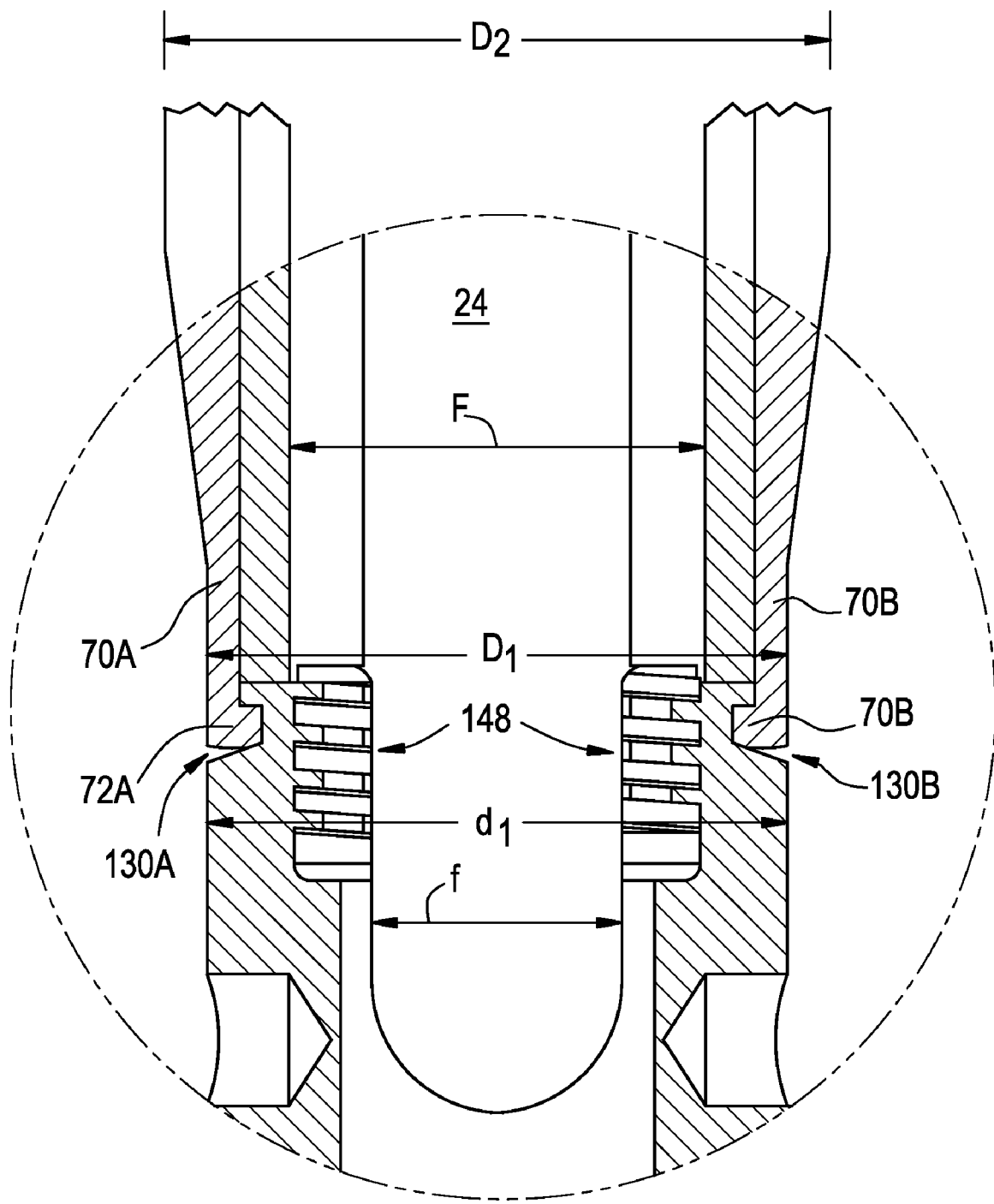
FIG. 7 is a side elevational view in cross-section of the distal end of the percutaneous access device of FIG. 1 coupled to the receiving member of the bone anchor assembly of FIG. 4.

Continuing to refer to FIGS. 1-5, the inner tube or sleeve 12 includes a proximal end 20, a distal end 22, and a lumen 24 extending between the proximal end 20 and the distal end 22. The lumen 24 extends the length of the inner tube 12 and defines a longitudinal axis 26 of the inner tube 12. The outer tube or sleeve 14 includes a proximal end 30, a distal end 32, and a lumen 34 extending between the proximal end 30 and the distal end 32. The lumen 34 may extend the length of the outer tube 14 and defines a longitudinal axis 36 of the outer tube 14. The inner tube 12 in positionable within the lumen 36 of the outer tube 14. In the exemplary percutaneous access device 10, the inner tube 12 is longitudinally adjustable with respect to the outer tube 14. For example, the inner tube 12 may adjustable from a first, proximal position, in which the distal end 22 of the inner tube 12 is positioned proximal to the distal end 32 of the outer tube 14 as illustrated in FIG. 3, and a second, distal position, in which the distal end 22 of the inner tube 12 is positioned proximate to the distal end 32 of the outer tube 14. In the exemplary embodiment, the distal end 22 of the inner tube 12 preferably contacts at least a portion of the bone anchor assembly when the inner tube 12 is in the second position, as illustrated in FIGS. 4 and 7 and as discussed in more detail below.

The exemplary percutaneous access device 10 may include an adjustment mechanism 40 that allows an operator to adjust the relative longitudinal position of the inner tube 12 and the outer tube 14. In the illustrated embodiment, for example, the adjustment mechanism 40 is a hollow, tubular shaped cap 41 having internal threads 42 that engage external threads 44 provided on the proximal end 30 of the outer tube 14. The threads 42, 44 allow the cap 41 to be longitudinal adjusted relative to the outer tube 14. In the exemplary embodiment, the inner tube 12 is connected to the cap 41 and, thus, can move with cap 41 as the cap 41 is advanced or withdrawn relative to the outer tube 14. For example, the proximal end 30 of the inner tube 12 of the exemplary embodiment may include one or more resilient tabs 46, one or more of which may have a projection 48 that seats within an annular grove provided on the interior surface of the cap 41 to thereby connect the proximal end 30 of the inner tube 12 to the cap 41. In the illustrated embodiment, two resilient tabs 46 are provided on opposite sides of the outer tube 14. The projection 48, in the exemplary embodiment, is sized to rotate with in the groove provided in the cap 41, thus allowing the cap 41 to rotate relative to the inner tube 12. The resilient tabs 46 are radially flexible to facilitate connection to and removal from the cap 41. One skilled in the art will appreciate that other configurations for connecting the inner tube 12 to the cap 41 are possible and are within the scope of the present disclosure.

The inner tube 12 may be inhibited from rotating with respect to the outer tube 14, limiting the relative motion of the inner tube 12 and the outer tube 14 to along the longitudinal axis 16 of the percutaneous access device. For example, one or more resilient tabs 56 may be provided on the inner tube 12 approximately midway between the proximal end 20 and the distal end 22 of the inner tube 12, although other positions are possible. In the illustrated embodiment, two resilient tabs 56 are provided on opposite sides of the outer tube 14. One or more of the resilient tabs 56 may include a projection 58 that is sized and shaped to seat within a longitudinal slot 54 provided in the outer sleeve 14. The resilient tab 56 can be radially flexible to facilitate insertion into and removal from the slot 54. The projection 58 can slide within the slot 54 and, thereby can limit the relative motion between the inner tube 12 and the outer tube 14 to along the longitudinal axis 16 of the percutaneous access device 10. One skilled in the art will appreciate that other configurations for connecting the inner tube 12 to the outer tube 14 are possible and are within the scope of the present disclosure.

The inner tube 12 may have one or more sidewall openings or slots 60 formed therein. In the illustrated exemplary embodiment, the inner tube 12 includes two opposed slots 60 that extend longitudinally from the distal end 22 of the inner tube 12. Like the inner tube 12, the outer tube 14 may have one or more sidewall openings or slots 62 formed therein. In the illustrated exemplary embodiment, the outer tube 14 includes two opposed slots 62 that extend longitudinally from the distal end 32 of the inner tube 12. The slots 60 and 62 can be used to facilitate positioning of a spinal fixation device, such as a rod or a plate, relative to one or more bone anchors. Methods and devices for spinal fixation element placement are disclosed in commonly owned, co-pending U.S. patent application Ser. No. 10/737.537, filed Dec. 16, 2003, entitled Method and Devices for Spinal Fixation Element Placement and commonly owned co-pending U.S. patent application Ser. No. 10/738,130, filed Dec. 16, 2003, entitled Method and Devices for Minimally Invasive Spinal Fixation Element Placement, both of which are incorporated herein in by reference. To facilitate positioning of a spinal fixation element, the slots 60 and the slots 62 are preferably aligned with one another along at least a portion of the longitudinal axis of the percutaneous access device 10. The width and length of the slot 60 and slot 62 may be varied depending on the particular methods, instruments, and fixation elements being employed. In one exemplary embodiment, for example, the length of the slots 60 and 62 is selected to span at least from the skin incision to the distal end of the inner tube 12 and the outer tube 14, respectively. In such embodiments, the slots 60 and 62 may be accessible from outside of the patient. In another exemplary embodiment, the length of the slots 60 and 62 is selected to span from the distal end of the inner tube 12 and the outer tube 14, respectively, to a point distal to the skin incision. In such embodiments, the slots 60 and 62 may be accessible only from the lumens of the inner and outer tubes.

In embodiments in which multiple slots are employed, the slots 60, 62 need not be similarly sized (width and/or length). For example, the one or more slots 60 may be sized differently than the one or more slots 62, the one or more of the slots 60 on the inner tube may be sized differently than other slots 60, and/or one or more of the slots 62 on the outer tube may be sized differently than other slots 62. Although the exemplary embodiment includes two opposing slots on the inner tube 12 and the outer tube 14, respectively, one skilled in the art will appreciate that any number of slots may be provided, e.g., no slots, one, two, three, etc. slots, may be provided depending on the method, instruments, and/or fixation element employed.

One skilled in the art will appreciate that the slots 60 and 62 are optional and that in certain embodiments slots may not be provided.

Referring to FIGS. 1-5 and 7, the percutaneous access device 10 is preferably releasably engageable to a bone anchor. In the exemplary embodiment, the outer tube 14 may be releasably engaged to a bone anchor, such as bone anchor assembly 100. For example, the outer tube 14 may be engaged to a bone anchor in a manner that allows the percutaneous access device 10 to be connected to the bone anchor 100 during use, e.g., during implantation and/or delivery and/or fastening of a spinal fixation element to the bone anchor, and allows the percutaneous access device to be disconnected from the bone anchor 100 at the conclusion of the procedure. Preferably, the percutaneous access device 10 can be disconnected remotely. For example, the exemplary embodiment, the percutaneous access device 10 can be disconnected from the bone anchor by manipulation of the proximal end of the percutaneous access device 10, as discussed in more detail below.

The distal end 32 of the outer tube 14 includes a pair of opposed longitudinally extending tabs 70A and 70B that may releaseable engage a bone anchor. In the exemplary embodiment, the tabs 70A and 70B are defined by the sidewalls of the outer tube 14 and are separated by slots 62A and 62B. In certain exemplary embodiments, the tabs 70A and 70B may be flexible and resilient in the radial direction to facilitate connection to a bone anchor. For example, the tabs 70A and 70B may be flexed apart in the radial direction from a first, relaxed position to facilitate advancement of the tabs longitudinally over a portion of the bone anchor. Once positioned about a portion of the bone anchor, the tabs 70A and 70B may provide a radially compressive force on the bone anchor as the tabs 70A and 70B attempt to return to the first, relaxed position. In other exemplary embodiments, including the exemplary percutaneous access device 10, the tabs 70A and 70B need not be flexible and resilient.

Figure 8:
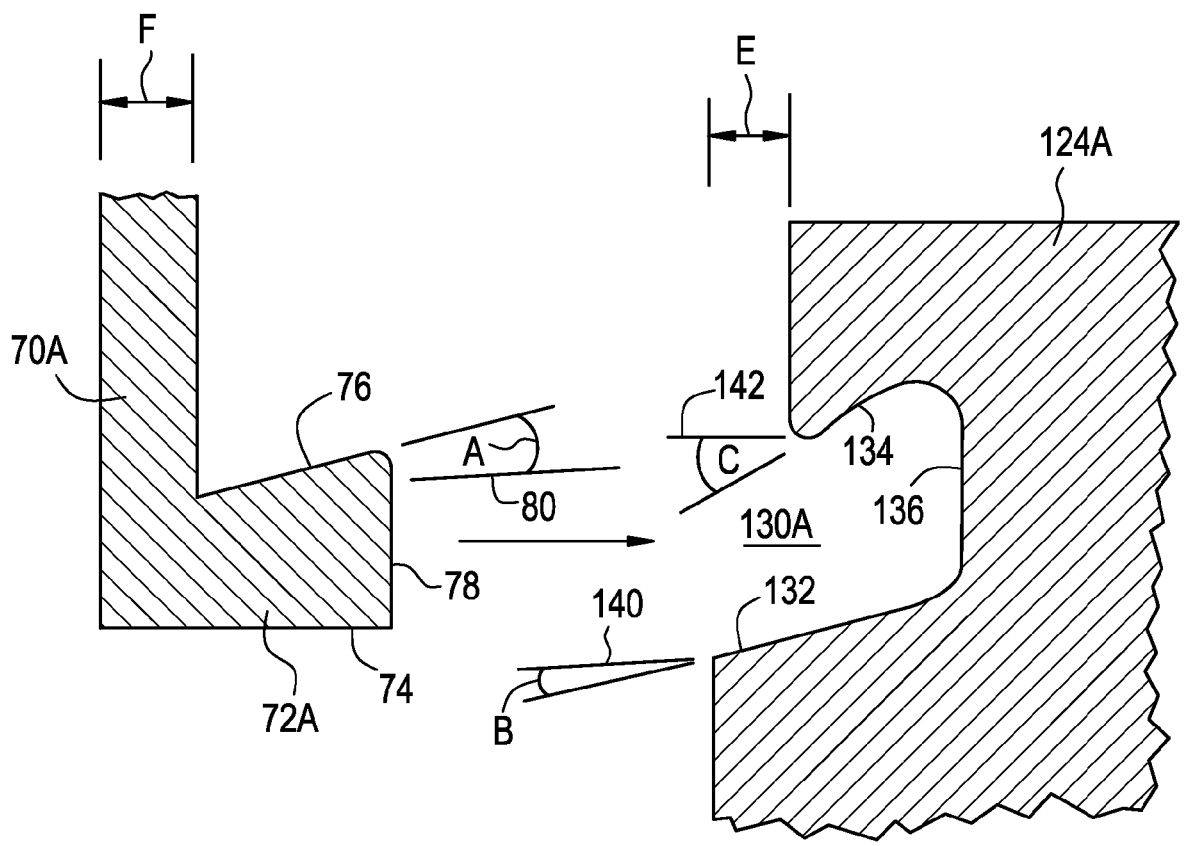
FIG. 8 is a side elevational view in cross-section of the distal end of the outer tube of the percutaneous access device of FIG. 1 and the receiving member of the bone anchor assembly of FIG. 4.
Figure 9:
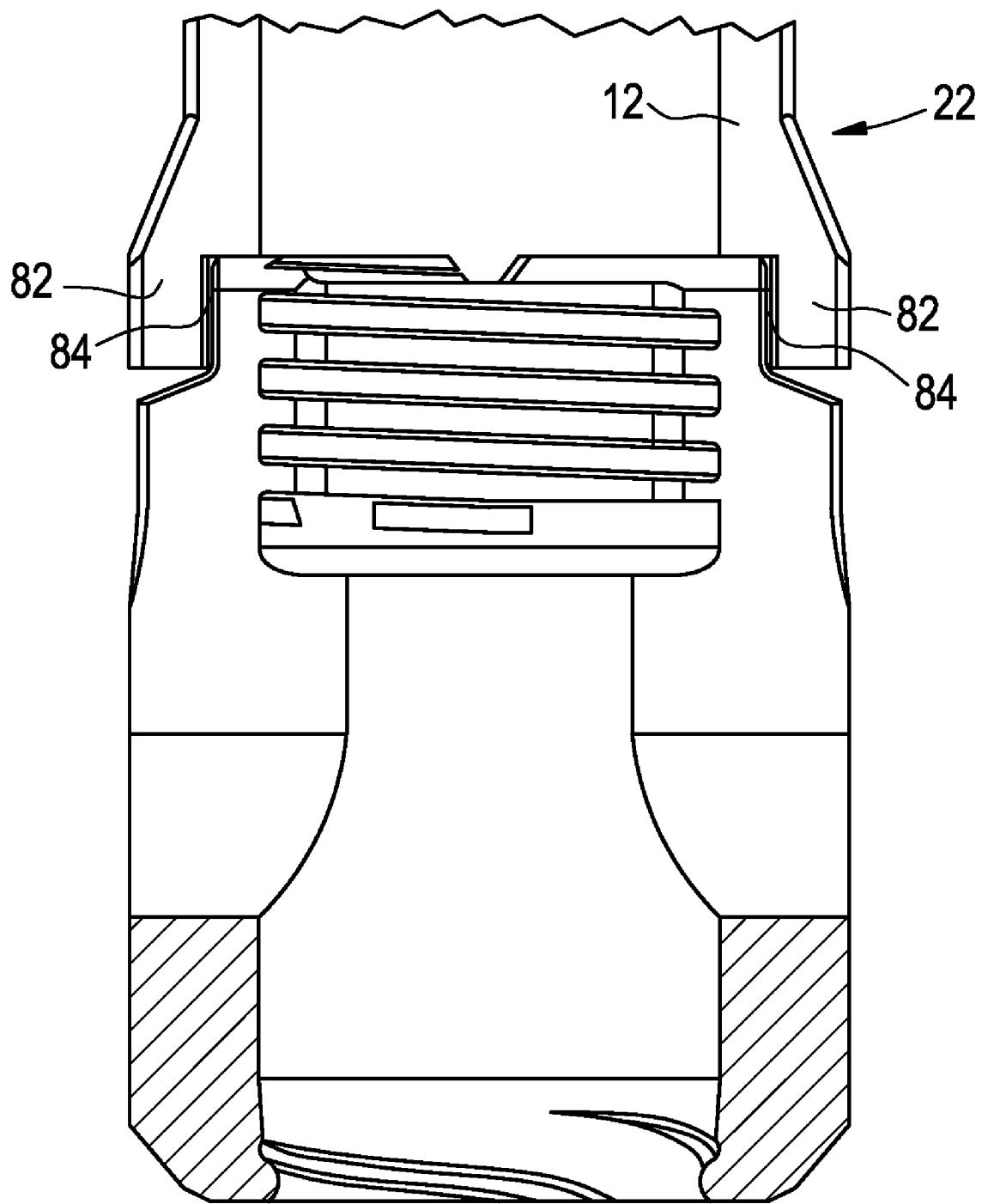
FIGS. 9 and 10 are side elevational views in cross section of the distal end of the inner tube of the percutaneous access device of FIG. 1 and the receiving member of the bone anchor assembly of FIG. 4.
Figure 10:
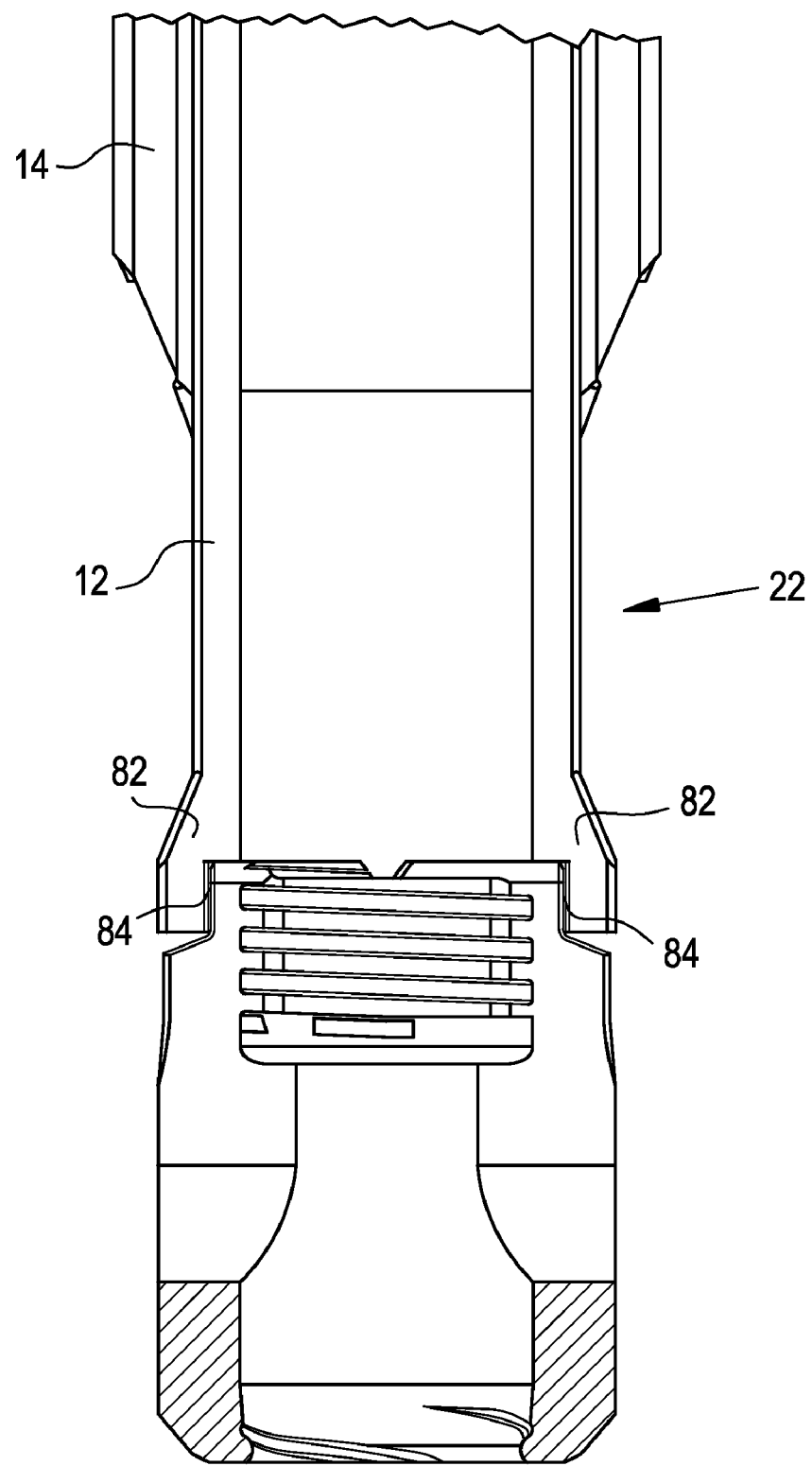

In the illustrated exemplary embodiment, each tab 70A and 70B may include one or more radially inward facing projection 72 that is sized and shaped to seat within an opening provided in a portion of the bone anchor. The size, shape and number of projections can be varied depending on, for example, the opening(s) provided on the bone anchor and type of connection desired. In the illustrated exemplary embodiment, for example, each projection 72A, 72B is generally arcuate in shape and has a cross section that is complementary to an arcuate groove 130 provided in the spinal fixation element receiving member 108 of the exemplary bone anchor assembly 100 described below. In particular, the projection 72A has a distal surface 74, a proximal surface 76, and a generally radially facing connecting surface 78 that spans between the distal surface 74 and the proximal surface 76, as shown in FIG. 8. In the illustrated embodiment, the distal surface 74 is generally oriented perpendicular to the longitudinal axis of the outer tube 14 and the connecting surface 78 is generally oriented parallel to the longitudinal axis of the outer tube 14 and perpendicular to the distal surface 74. One or both of the proximal surface 76 and the distal surface 74 may be oriented at an angle other than perpendicular to the longitudinal axis of the outer tube 14. For example, the proximal surface 76 may be oriented at an angle A to an orthogonal line 80, which is oriented perpendicular to the longitudinal axis of the outer tube 14. In the exemplary embodiment, the angle A may be approximately 5° to approximately 30° and is preferably approximately 20°. The distal surface 74 and the proximal surface 76 may be oriented at the same angle or, as in the exemplary embodiment, may be oriented at different angles.

Referring to FIGS. 2, 3, 4, 7, 9 and 10, the distal end 22 of the inner tube 12 may include a contact surface 81 that contacts at least a portion of a bone anchor when the inner tube 12 is in the second position. In the illustrated exemplary embodiment, for example, the distal end 22 of the inner tube 12 may have two opposing generally arcuate contact surfaces 81. The contact surfaces 81, in the exemplary embodiment, are oriented approximately perpendicular to the longitudinal axis of the inner tube 12. In the illustrated exemplary embodiment, the contact surfaces 81 are configured to contact a generally arcuate contact surface provided on the proximal end of the receiving member of the exemplary bone anchor assembly 100. Preferably, the contact surface 81 is complementary in size, shape, and orientation to the contact surface on the bone anchor. One skilled in the art will appreciate that the configuration of the contact surface 81, e.g., number, size, shape, and orientation of the contact surface 81, may be varied to, for example, suit the bone anchor being employed.

The distal end 22 of the inner tube 12 and/or the distal end 32 of the outer tube 14 may be configured to inhibit rotation of the bone anchor assembly relative to the percutaneous access device 10. For example, the distal end 22 of the inner tube may include one or more finger-like extensions 82 that extend approximately axially from the distal end 22 of the inner tuber 12 and engage a bone anchor to inhibit rotation of the bone relative to the percutaneous access device. For example, one or more of the extensions 82 may seat within a groove, recess, slot, or similar structure provided in the bone anchor. Alternatively, one of more of the extensions 82 may include a contact surface 84 for contacting an axially extending surface of the bone anchor, as in the case of the exemplary embodiment and as discussed in detail below.

Figure 5:
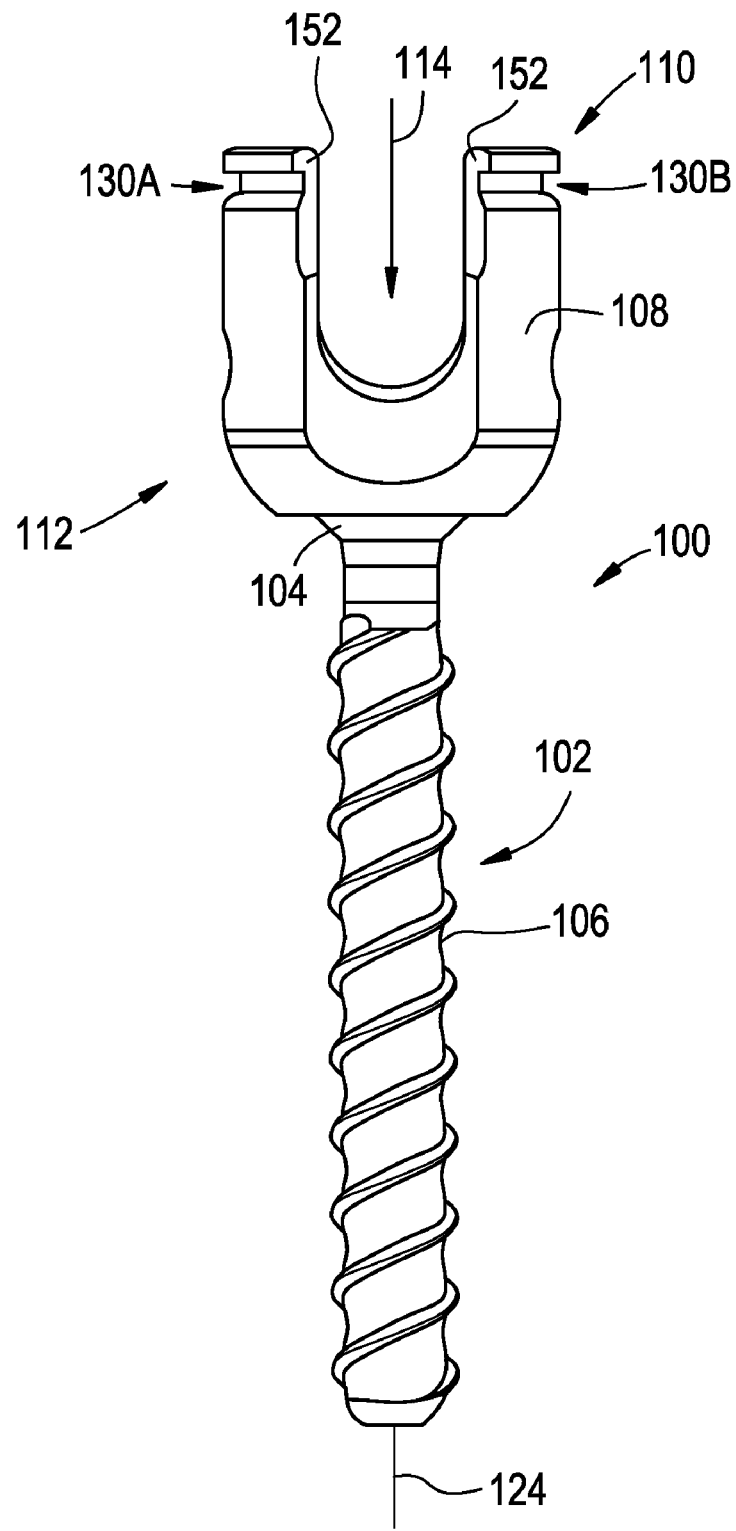
FIG. 5 is a side elevational view of the bone anchor assembly of FIG. 4.
Figure 6:
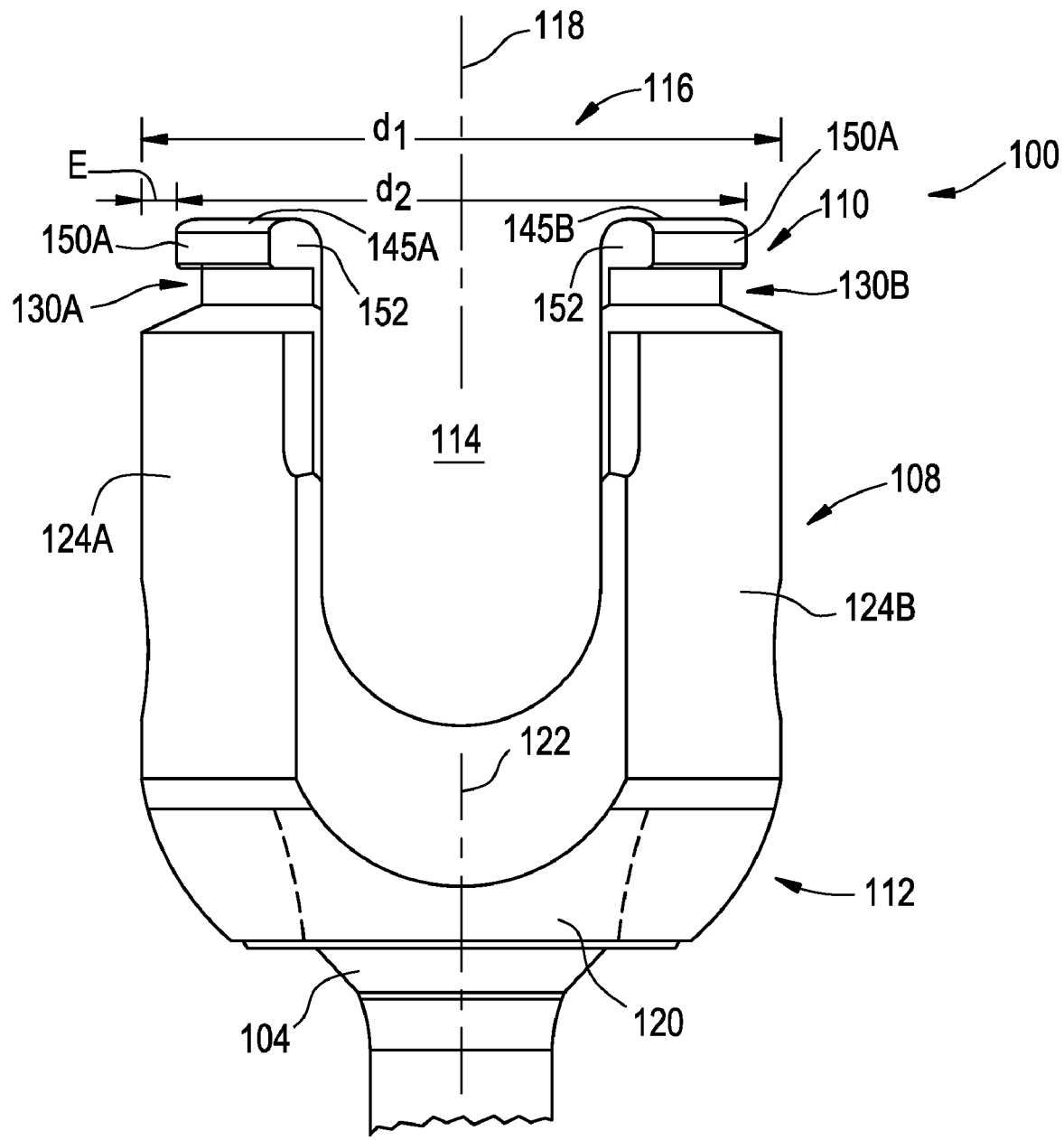
FIG. 6 is a side elevational view of the receiving member of the bone anchor assembly of FIG. 4.

FIGS. 5-6 illustrate an exemplary embodiment of a bone anchor assembly 100 that is particularly suited for use with the exemplary percutaneous access device 10 described. One skilled in the art will appreciate, however, that the percutaneous access devices disclosed herein are not limited to use with the exemplary bone anchor assembly 100 but instead may be configured for use with any type of bone anchor, e.g., bone screw or hook; mono-axial or polyaxial. Exemplary bone anchor assembly 100 includes a bone screw 102, such as a pedicle screw, having a proximal head 104 and a distal bone engaging portion 106, which in the illustrated exemplary embodiment is an externally threaded screw shank. The exemplary bone screw assembly 100 also includes a receiving member 108 that is configured to receive and couple a spinal fixation element, such as a spinal rod or spinal plate, to the bone anchor assembly 100.

The receiving member 108 may be coupled to the bone anchor 102 in any well-known conventional manner. For example, the bone anchor assembly may be poly-axial, as in the present exemplary embodiment in which the bone anchor 102 may be adjustable to multiple angles relative to the receiving member 108, or the bone anchor assembly may be mono-axial, e.g., the bone anchor 102 is fixed relative to the receiving member 108. An exemplary poly-axial bone screw is described U.S. Pat. No. 5,672,176, incorporated herein by reference. In mono-axial embodiments, the bone anchor 102 and the receiving member may be coaxial or may be oriented at angle with respect to one another. In poly-axial embodiments, the bone anchor may biased to a particular angle or range of angles to provide a favored angle the bone anchor. Exemplary favored-angle bone screws are described in U.S. Patent Application Publication No. 2003/0055426 and U.S. Patent Application Publication No. 2002/0058942, both of which are incorporated herein by reference.

The receiving member 108 of the illustrated exemplary embodiment includes a proximal end 110, a distal end 112, and a recess or slot 114 for receiving a spinal fixation element such as a spinal rod. The proximal end 110 of the receiving member 108 has a first bore 116 defining a first bore axis 118. The recess 114 communicates with the first bore 116 such that a spinal fixation element may be positioned through the first bore 116 into the recess 114. The distal end 112 has a second bore 120 opposite the second bore 116 and defining a second bore axis 122. The second bore axis 122 is designed to receive the head 104 of the bone anchor 102 to couple the bone anchor 102 to the receiving member 108. In the illustrated exemplary embodiment, the head 104 is seated within the second bore 116. As the exemplary illustrated embodiment of the bone anchor assembly is poly-axial, the bone anchor 102 is free to rotate relative to the receiving member 108 such that the longitudinal axis 124 of the bone anchor 102 is positionable at an angle relative to the second bore axis 120. The second bore 116 may be conically shaped to facilitate adjustment of the bone anchor 102 relative to the receiving member 108. In favored-angled embodiments, the second bore axis 122 may be positioned at an angle (other than 0°) to the first bore axis 118. In the illustrated embodiment, the first bore axis 118 and second bore axis 122 are coaxial. In the exemplary embodiment, the receiving member 108 has a generally U-shaped cross-section defined by two legs 124A and 124B separated by recess 114. Each leg 124A, 124B is free at the proximal end 110 of the receiving member 108.

The receiving member 108 may be configured to receive a closure mechanism that locks a spinal fixation element within the recess 114. The closure mechanism may be a cap that is advanceable through the first bore 116 of the receiving member 108 and seats against the spinal fixation element. For example, the cap may have external threads that engage internal threads 148 provided in the receiving member 108, e.g., on the legs 124A, B, as in the exemplary embodiment. Any type of conventional closure mechanism may be employed, including, for example, non-threaded caps, multi-component closure mechanisms, and/or external caps.

The receiving member 108 of the exemplary bone anchor assembly 100 is configured to be releasably connected to an instrument such as the exemplary percutaneous access device 10 described above. For example, the receiving member 108 may include at least one groove 130 that is configured to receive a portion of an instrument to releasably connect the instrument to the bone anchor assembly. The size, shape, position, and number of grooves can be varied depending on, for example, the instrument employed and the type of connection desired. In certain embodiments, for example, at least one arcuate groove 130 may be provided on an exterior surface of the proximal end 110 of the receiving member 108. In other exemplary embodiments, at least one arcuate groove may be provided on an interior surface of the proximal end 110 of the receiving member 108. In the illustrated exemplary embodiment, each leg 124A and 124B may be provided with an arcuate groove 130A, 130B, respectively, at the free, proximal end of the leg 124A, 124B. The grooves 130A, 130B may extend about a portion or all of the circumference of the proximal end of each leg 124A, 124B. Each groove 130A, 130B may have size and shape that is complementary in size and shape to a projection provided on the instrument. For example, in the illustrated exemplary embodiment, the each groove 130A, 130B may be arcuate and may have a cross-section complementary to the cross-section of a projection 72A, 72B provided on the tabs 70A, 70B of the outer sleeve 14. In particular, groove 130 may have a distal surface 132, a proximal surface 134 and an interconnecting surface 136 that spans between the distal surface 132 and the proximal surface 134, as illustrated in FIG. 8. The distal surface 132 and/or the proximal surface 134 may be oriented to facilitate insertion of a projection into the grove 130 and/or to inhibit undesirable separation of the projection from the groove 130. In the illustrated exemplary embodiment, for example, the distal surface 132 may be generally oriented at an angle B to an orthogonal line 140, which is oriented perpendicular to the longitudinal axis of the receiving member 108, to facilitate insertion of the projection into the groove. In the exemplary embodiment, the angle B may be approximately 0° to approximately 45° and preferably approximately 30° to 40°. In the illustrated exemplary embodiment, the proximal surface 134 may be oriented at an angle other than perpendicular to longitudinal axis of the receiving member 108 to inhibit separation of the projection from the groove 130, particularly in radial direction. For example, the proximal surface 134 may be oriented at an angle C to an orthogonal line 142, which is perpendicular to the longitudinal axis of the receiving member 108. In the exemplary embodiment, the angle C may be approximately 5° to approximately 30° and is preferably approximately 20°. The distal surface 132 and the proximal surface 76 may be oriented at the same angle or, as in the exemplary embodiment, may be oriented at different angles. The grooves 130A and 130B, as well as any additional grooves, may have similar cross-sectional geometries, as in the case of the illustrated exemplary embodiment, or may have distinct geometries.

Referring to FIGS. 7 and 8, the proximal surface 76 of each projection 72 may be oriented at an angle A that is approximately equal to the angle C of the proximal surface 134 of the corresponding groove. In one preferred embodiment, for example, angle A and angle C are each approximately 20°. One skilled in the art will appreciate that angle A and angle C need not be approximately equal but instead, may be separate, distinct angles.

The proximal end 110 of the receiving member 108 may include one or more contact surfaces that may be contacted by an instrument such as the percutaneous access device 10. In the illustrated exemplary embodiment, for example, the proximal end of each leg 124A, 124B may include one or more generally arcuate, proximally facing contact surfaces 145.

The outer diameter of the percutaneous access device may be selected to be approximately equal to the outer diameter of the bone anchor to facilitate insertion of the bone anchor into the body through a percutaneous pathway of minimal size. For example, in the illustrated exemplary embodiment, the outer diameter of the outer tube 14, indicated by line $D_1$ in FIG. 7, at at least the distal end 32 of the outer tube 14, is approximately equal to, or less than, the outer diameter of the receiving member 108, indicated by line $d_1$ in FIGS. 6 and 7. For example, the diameter of the outer tube 14 may taper from a proximal diameter $D_2$ to a distal diameter $D_1$ at the distal end 32 of the outer tube 14. Alternatively, the outer diameter of the outer tube 14 may be approximately equal to, or less than, the outer diameter of the receiving member 108 along the entire length of the outer tube 14. To accommodate the outer tube 14, the proximal end 110 of the receiving member 108 may have a diameter $d_2$ that is less than the diameter $d_1$ of a distal section of the receiving member 108, as illustrated in FIG. 6. For example, the diameter $d_2$ proximal to the grooves 130A, B may be less than the diameter $d_1$ of the receiving member 108 to provide a reduced diameter portion 150 at he proximal end 130 of the receiving member. The distance between the exterior surface of reduced diameter portion 150 and the exterior surface of the receiving member 108, indicated by line E in FIGS. 6 and 8, is preferably greater than or approximately equal to the radial thickness of a tab 70A, 70B, as indicated by line F in FIG. 8.

Figure 11A:
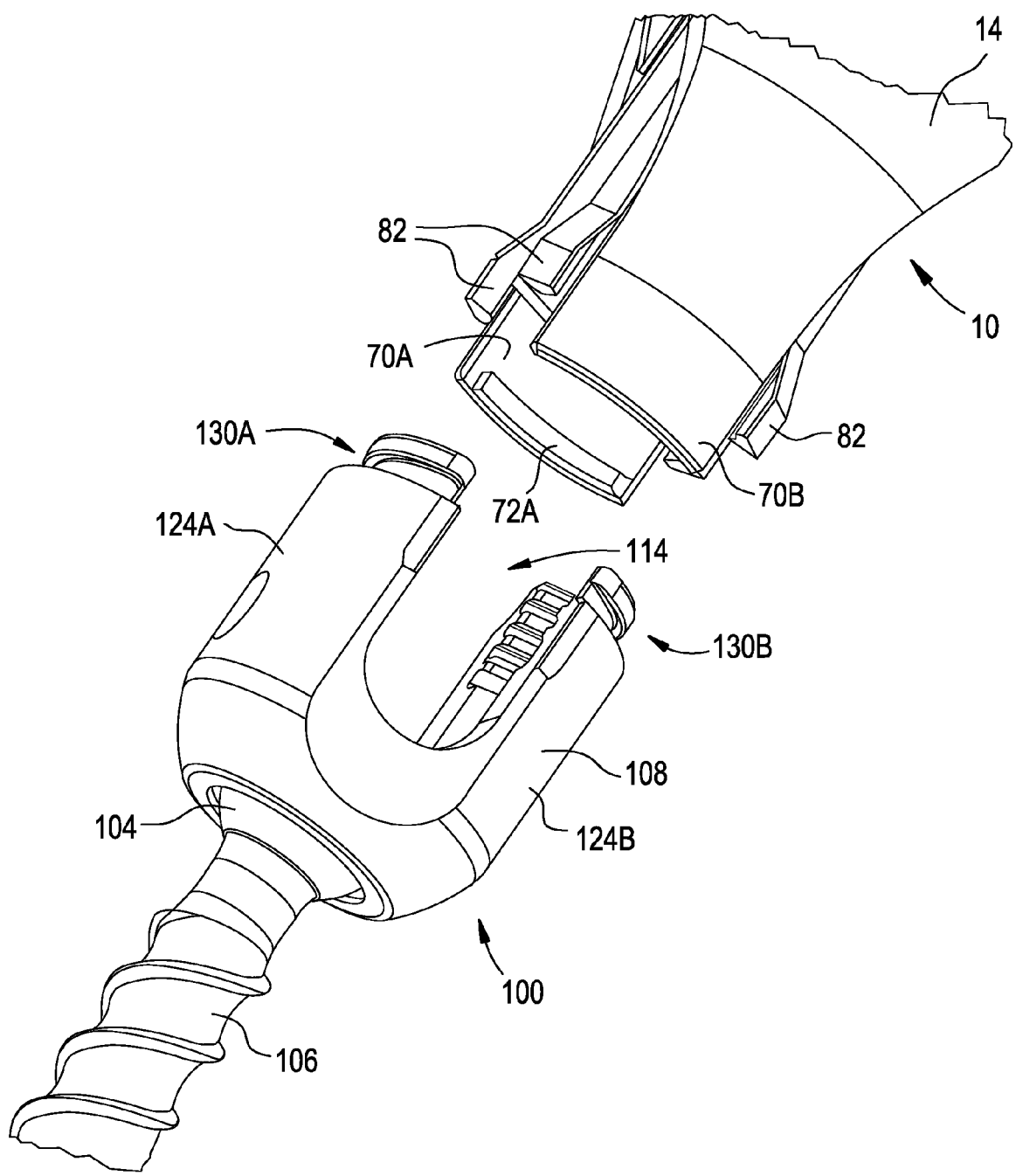
FIGS. 11A-11D are perspective views of the distal end of the percutaneous access device of FIG. 1 and the receiving member of the bone anchor assembly of FIG. 4, illustrating exemplary steps for releasably coupling the distal end of the percutaneous access device to the receiving member of the bone anchor assembly.
Figure 11B:
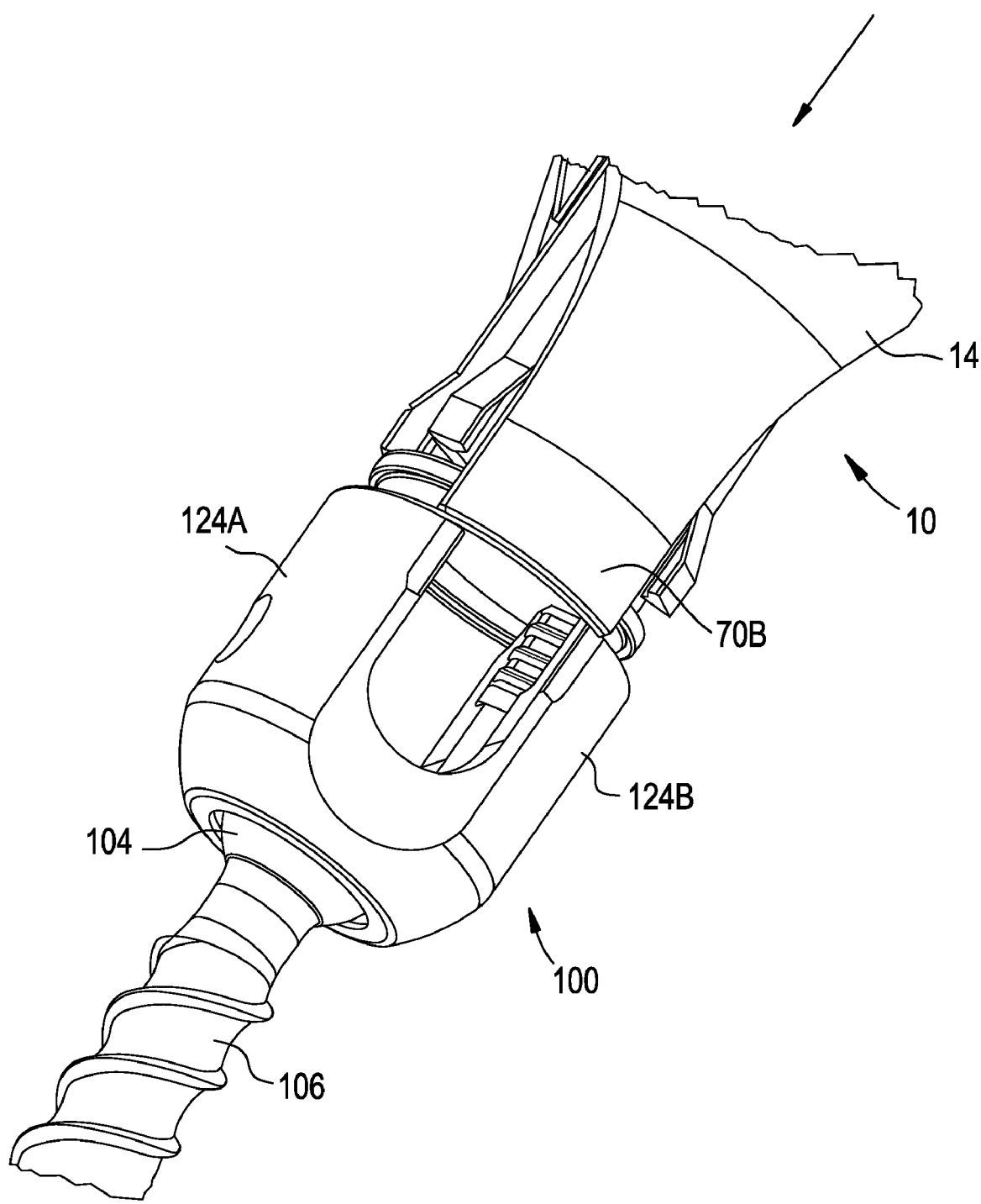
Figure 11C:
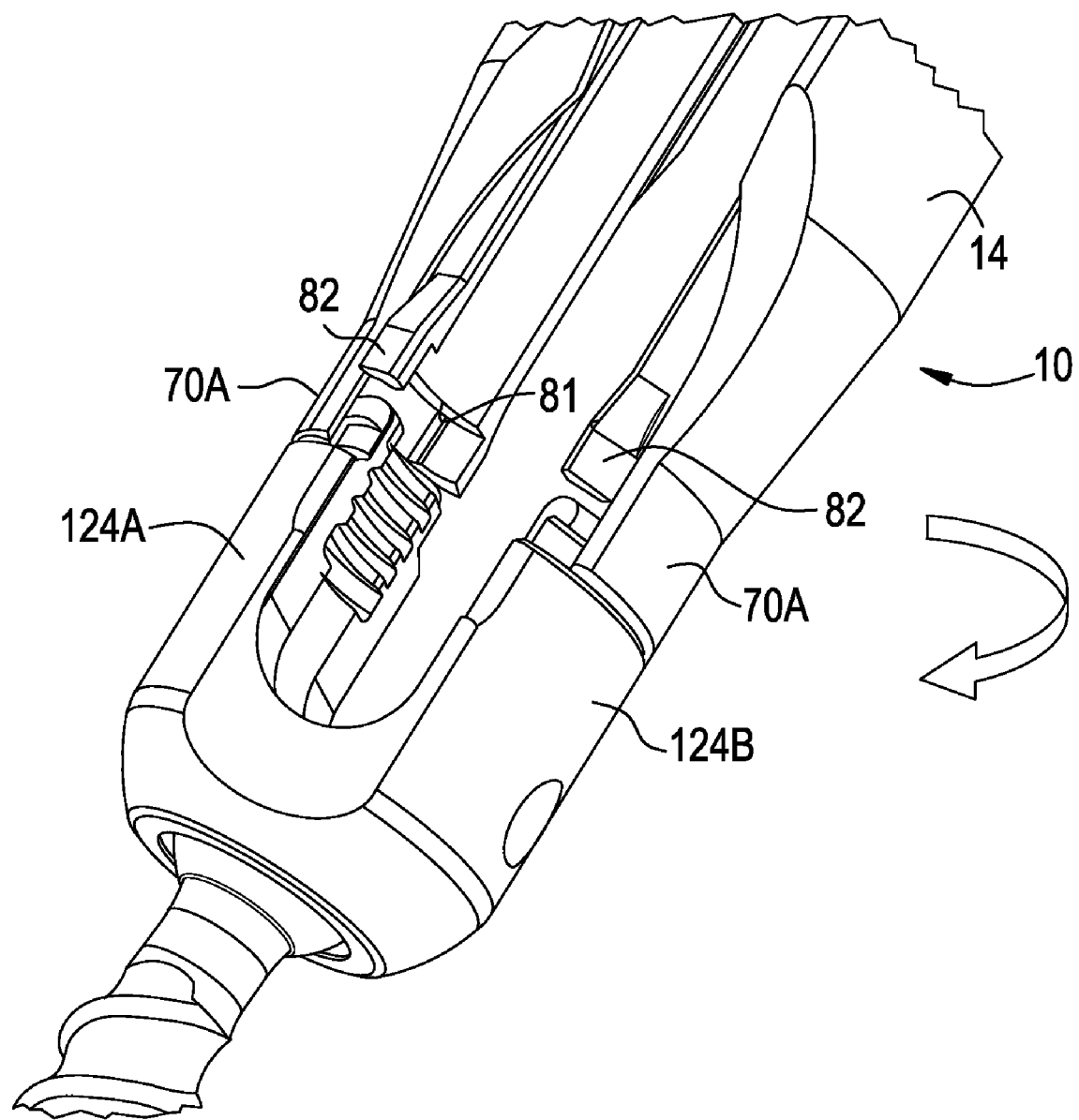

To facilitate delivery of devices to the bone anchor assembly through the percutaneous access device 10, the inner diameter of the lumen 24 of the inner tube 12, indicated by line F in FIG. 7, at at least the distal end of the inner tube 12, may be greater than or approximately equal to the inner diameter of at least a portion of the receiving member, indicated by line f in FIG. 7. [58] Exemplary operation of the percutaneous access device 10 with the exemplary bone anchor assembly will be described with reference to FIGS. 11A-11D. To releasably connect the percutaneous access device 10, the distal end 32 of the outer tube 14 is oriented such that tabs 70A and 70B are aligned with recess 114, as illustrated in FIG. 11A. The percutaneous access device 10 is advanced distally until each tab 70A, 70B is positioned between the legs 124A and 124B, as illustrated in FIG. 11B. The percutaneous access device 10 may be rotated about its longitudinal axis 16 to rotate projections 72A, 72B into grooves 103B, 130A, respectively, as illustrated in FIG. 11C. The inner tube 12 may be advanced distally along the longitudinal axis 16 of the percutaneous access device 10 from the first, proximal position, illustrated in FIGS. 11A-C, to the second, distal position, illustrated in FIG. 11D, in which the contact surfaces 81 of the inner tube 12 contact the contact surfaces 145A, 145B provided on the proximal end of the receiving member of the exemplary bone anchor assembly 100, to thereby releasably connect the percutaneous access device 10 to the bone anchor assembly 100. The contact surface 84 of one or more of the extensions 82 may engage the axial extending contact surfaces 152 (FIGS. 5 and 6) to inhibit rotation between the percutaneous access device and the bone anchor assembly.

The percutaneous access device 10 may be connected to the exemplary bone anchor assembly 100, or another bone anchor assembly, before implantation of the bone anchor assembly or after the bone anchor assembly is implanted into the patient's body.

Figure 11D:
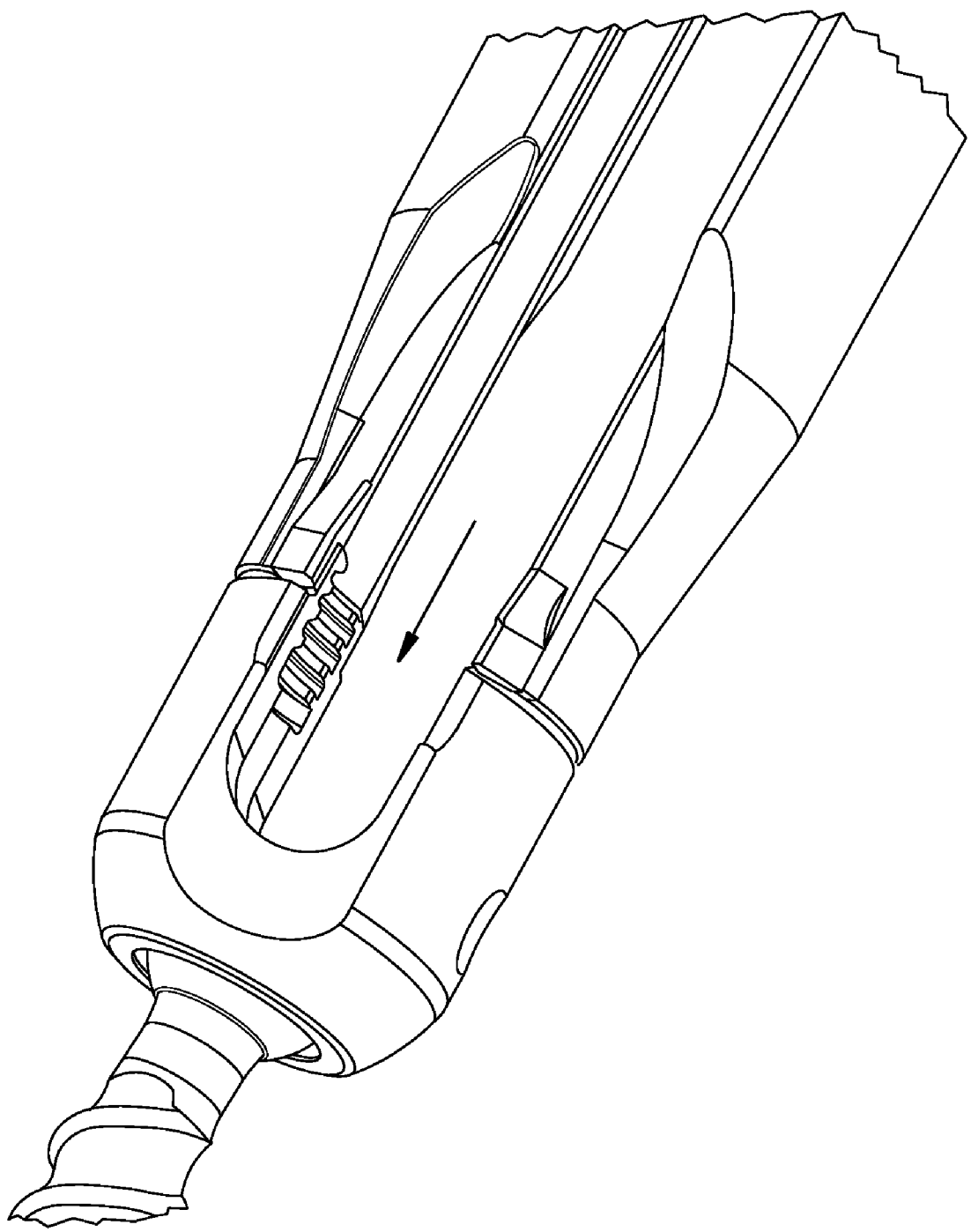
Figure 12:
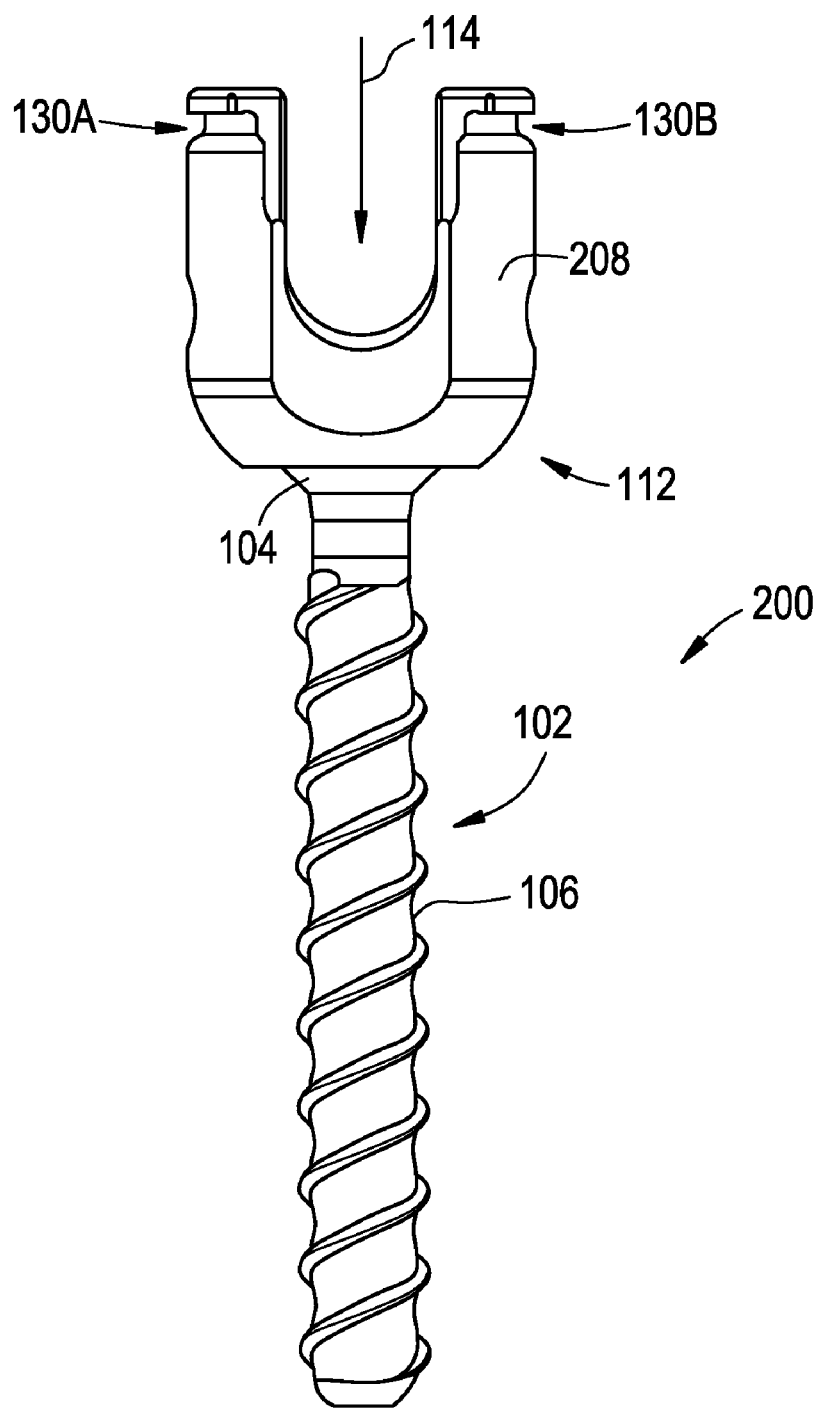
FIG. 12 is a side elevational view an another exemplary embodiment of a bone anchor assembly.
Figure 13:
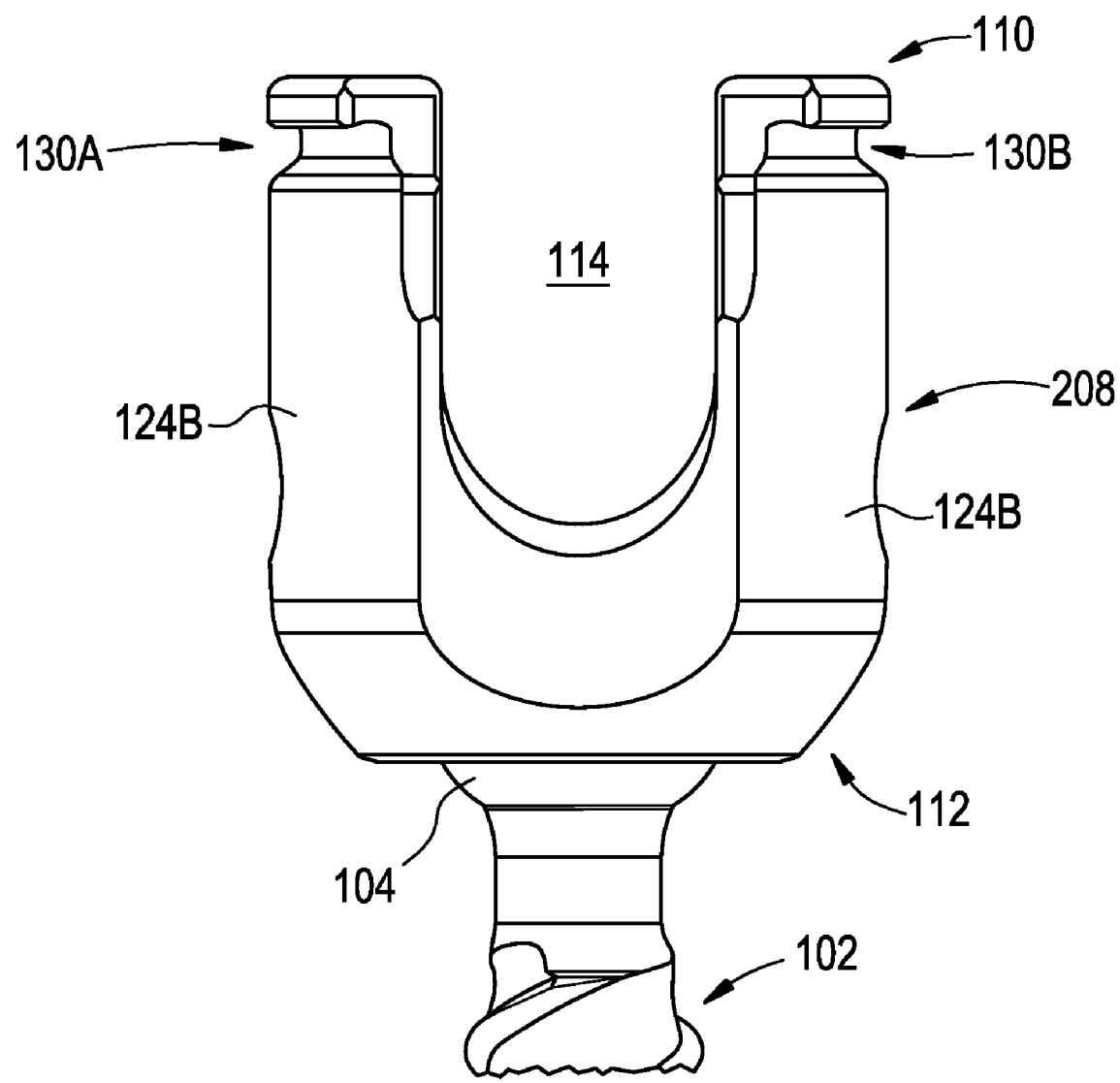
FIG. 13 is a side elevational view of the receiving member of the bone anchor assembly of FIG. 12.

Once the percutaneous access device 10 is releasably connected to the bone anchor assembly 100 as illustrated in FIGS. 1 and 11D, the percutaneous access device 10 may provide a percutaneous pathway between the skin incision and the bone anchor 100 that facilitates delivery of instruments, spinal fixation elements, and/or components of the bone anchor assembly, such as the closure mechanism, to the bone anchor assembly 100. In the illustrated exemplary embodiment, for example, the lumen 24 provides a pathway to the first bore 116 of the receiving member 108 of the bone anchor assembly 100, that may allow a closure mechanism, such as a threaded cap, to be delivered to the receiving member 108 of the bone anchor assembly and/or may allow a screw driver or the like to be advanced into engagement with the head 104 of the bone anchor 102. Moreover, in the illustrated exemplary embodiment, the slots 60 of the inner tube and the slots 62 of the outer tube 14 may be aligned with the recess 114 provided in the receiving member 108. Alignment of the slots 60 and 62 with the recess 114 facilitates the delivery of a spinal fixation element to the bone anchor assembly. Exemplary methods and devices for delivering a spinal fixation element to a bone anchor assembly are described in commonly owned, co-pending U.S. patent application Ser. No. 10/737.537, filed Dec. 16, 2003, entitled Method and Devices for Spinal Fixation Element Placement and commonly owned co-pending U.S. patent application Ser. No. 10/738,130, filed Dec. 16, 2003, entitled Method and Devices for Minimally Invasive Spinal Fixation Element Placement, each of which is incorporated herein in by reference.

The percutaneous access device 10 may be released from the bone anchor by rotating the percutaneous access device 10 about its longitudinal axis 16 and retracting the device 10 distally.

Figure 14:
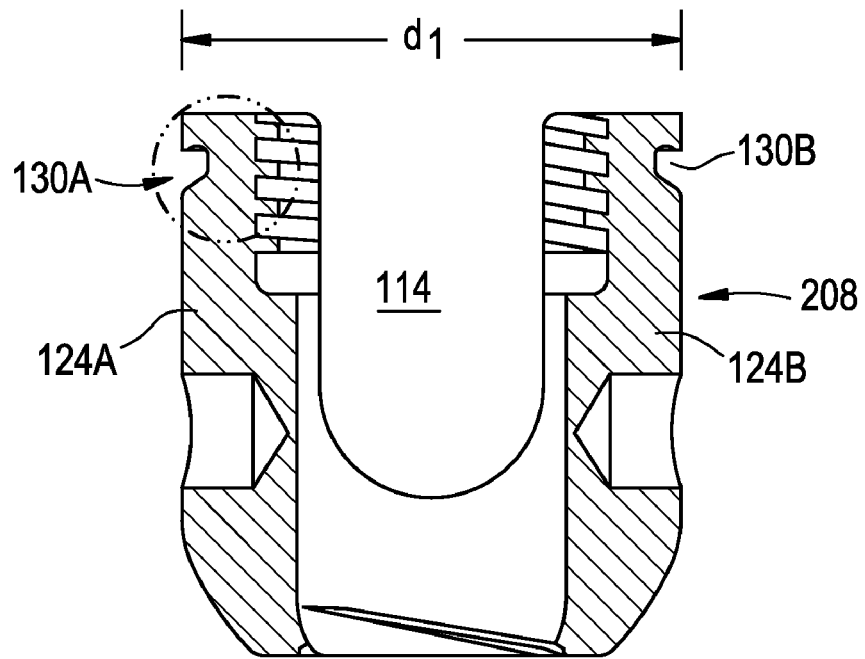
FIG. 14 is a side elevational view in cross section of the receiving member of the bone anchor assembly of FIG. 12.
Figure 15:
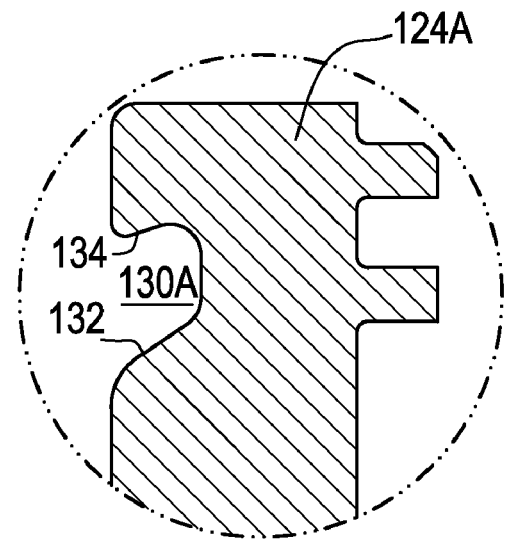
FIG. 15 is a side elevational view in cross section of an arcuate groove of the receiving member of the bone anchor assembly of FIG. 12.
Figure 16:
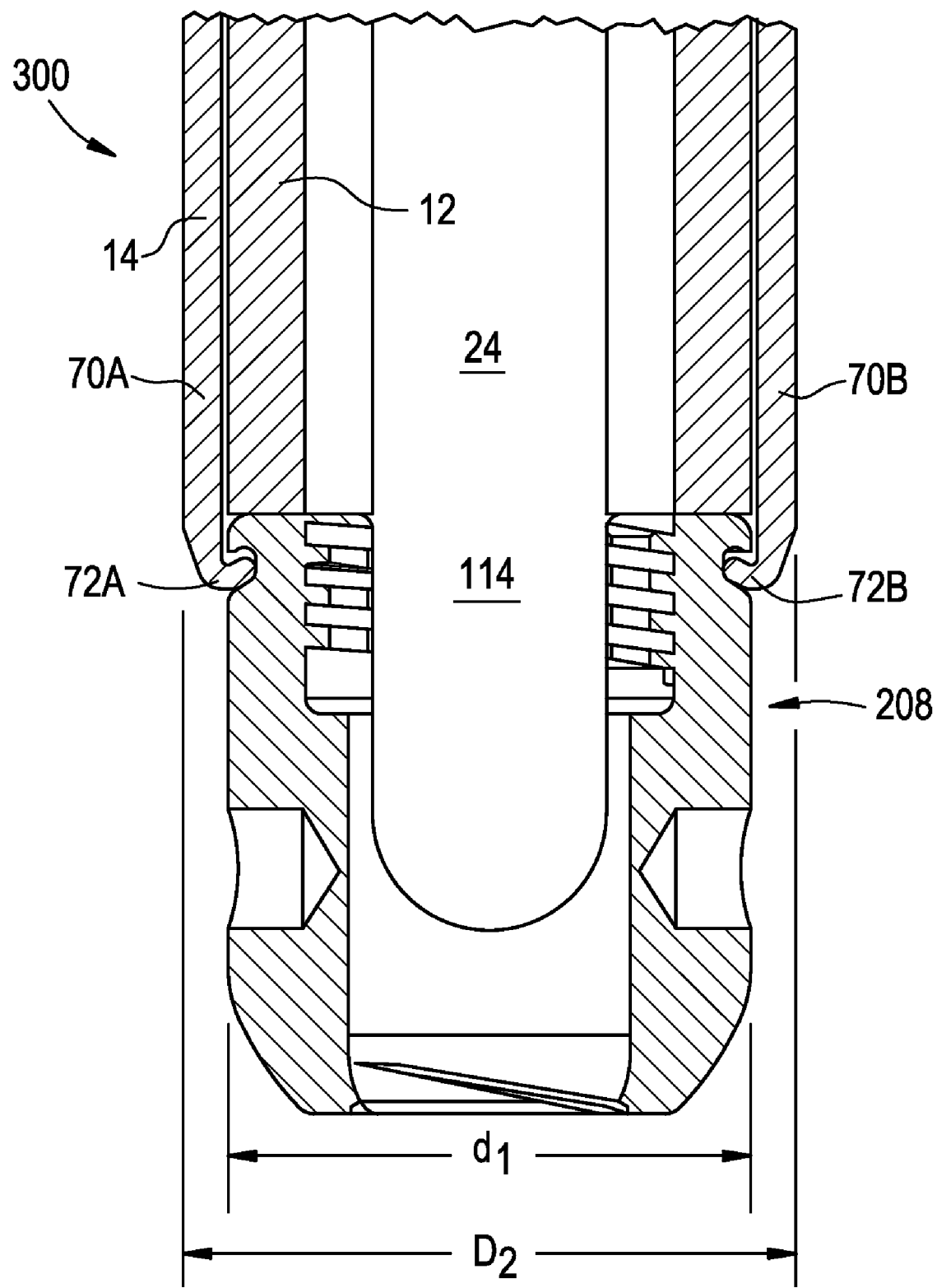
FIG. 16 is a side elevational view in cross-section of the distal end of the another exemplary embodiment of a percutaneous access device coupled to the receiving member of the bone anchor assembly of FIG. 12.

FIGS. 12-16 illustrate an alternative exemplary embodiment of a bone anchor assembly 200 and an exemplary percutaneous access device 300 that may be configured to releasably engage the bone anchor assembly 200. The exemplary bone anchor assembly 200 is analogous in construction to the exemplary bone anchor assembly 10 described above, except that the receiving member 208 of the bone anchor assembly 200 has a generally constant outer diameter $d_1$, as illustrated in FIGS. 14 and 16, at the proximal end 110 thereof, and, thus, lacks the reduced diameter portion 150 of bone anchor assembly 100. As a result, the outer diameter of the distal end 32 of the outer tube 14 of the exemplary percutaneous access device 300, indicated by line $D_2$ in FIG. 16, may be approximately equal to or, as in the illustrated embodiment, may be greater than the diameter $d_1$ of the proximal end 110 of the receiving member 208. The outer diameter of the outer tube 14 may be constant, as in the illustrated exemplary embodiment, or may vary along the length of the outer tube 14.

Figure 17A:
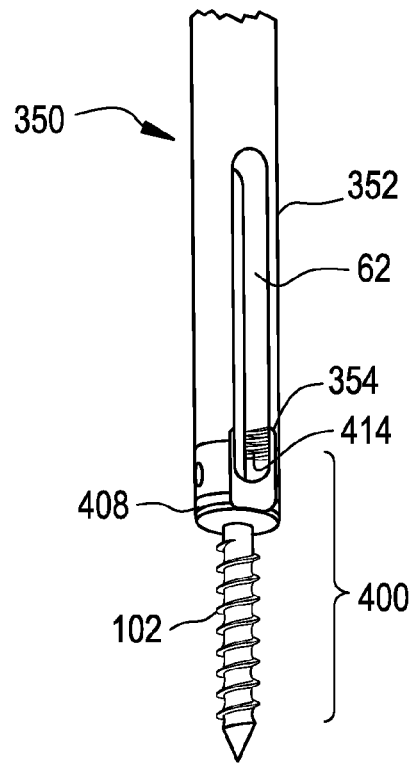
FIGS. 17A and 17B are perspective views of an alternative embodiment of a percutaneous access device and a bone anchor assembly, illustrating a threaded connecting between the percutaneous access device and the bone anchor assembly.
Figure 17B:
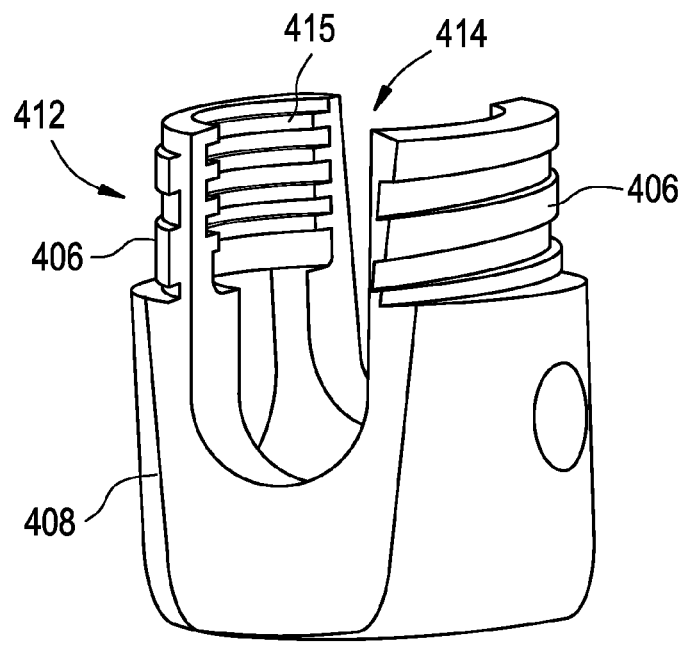

FIGS. 17A and 17B illustrate an alternative embodiment of a percutaneous access device 350 and a bone anchor assembly 400, in which the percutaneous access device and the bone anchor assembly are interconnected by threads. For example, the percutaneous access device 350 may have an outer tube 352 having a distal end 354 provided within internal threads that releasably engage external threads 406 provided on the proximal end 412 of the receiving member 408 of the bone anchor assembly 400. Preferably, the external threads 406 are clocked to facilitate alignment of the grooves 62, if any, provided on the outer tube 14 with the recess 414 provided in the receiving member 408. In the illustrated exemplary embodiment, the percutaneous access device 350 includes a single tube, outer tube 352; an inner tube may be provided but is not necessary.

Figure 18A:
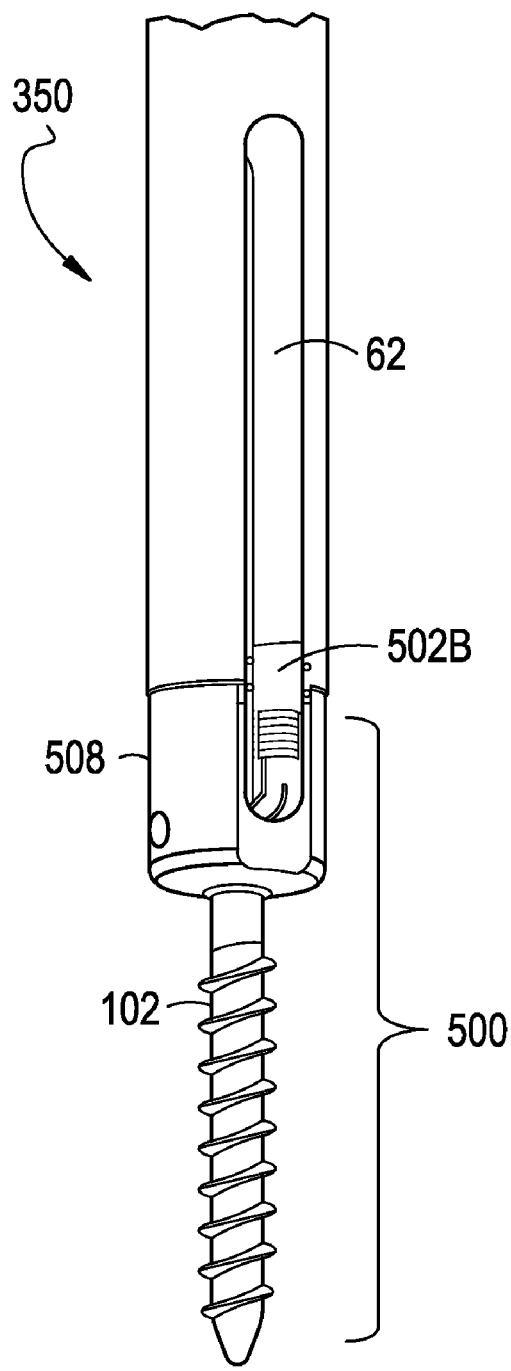
FIGS. 18A and 18B are perspective views of an alternative embodiment of a percutaneous access device and a bone anchor assembly, illustrating a plurality of externally threaded removable tabs for releasable engagement with an instrument such as a percutaneous access device.
Figure 18B:
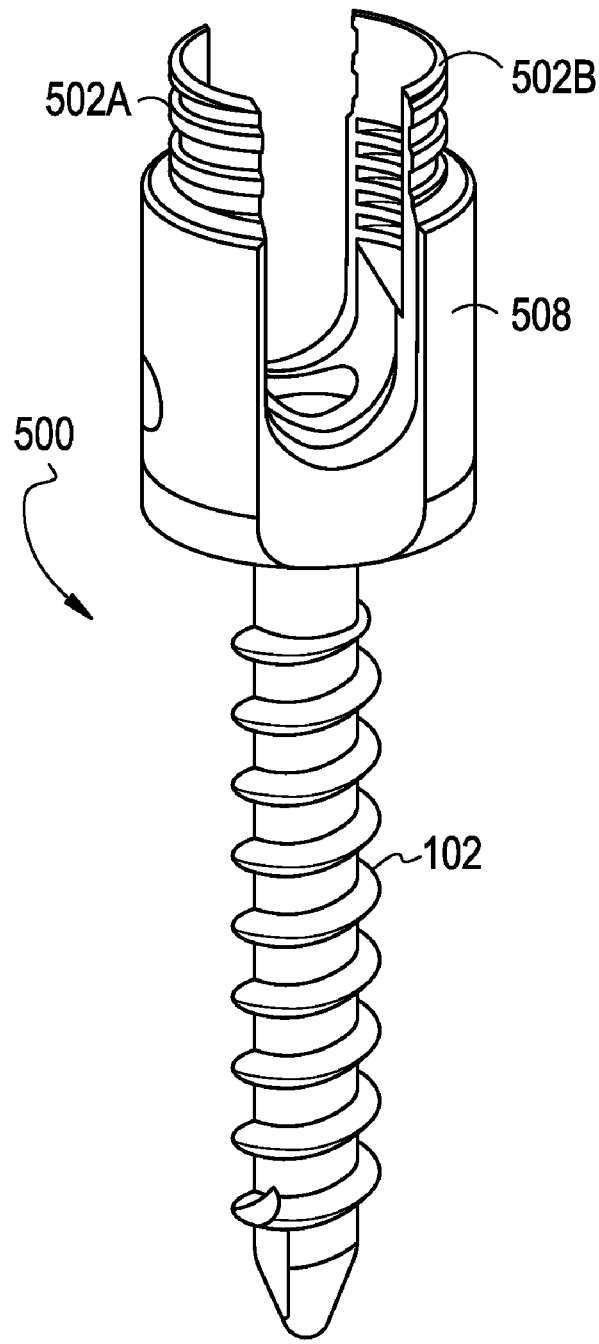
Figure 19A:
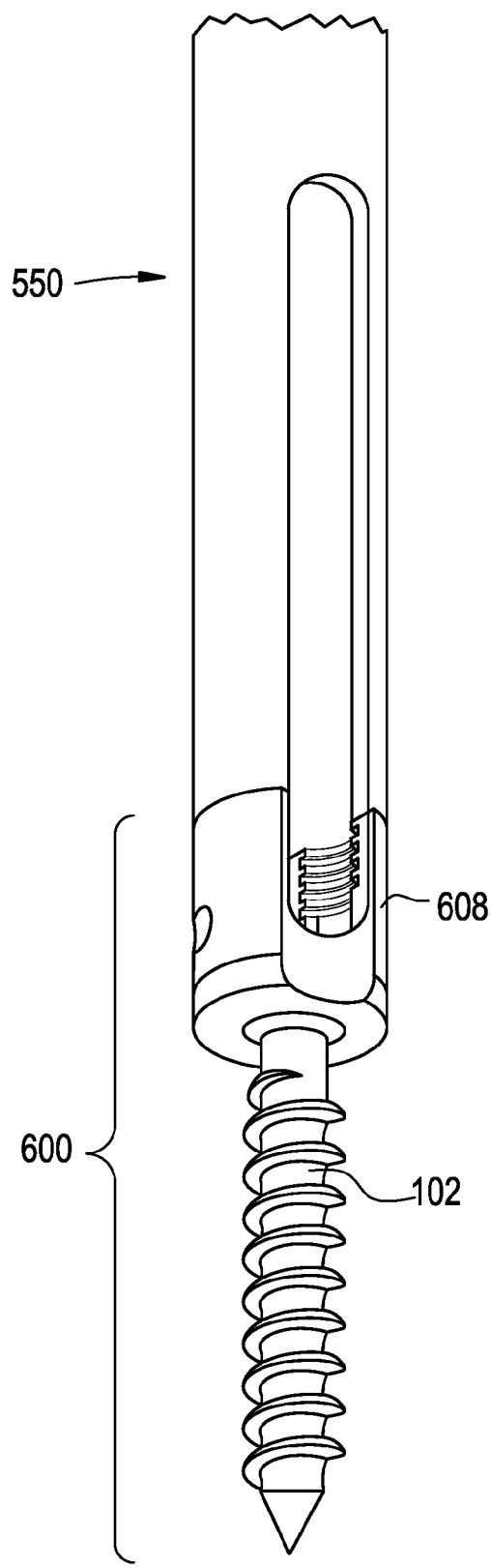
FIGS. 19A-19D are perspective views of an alternative embodiment of a percutaneous access device and a bone anchor assembly, illustrating the percutaneous access device and the bone anchor assembly interconnected by one or more internal wires.
Figure 19B:
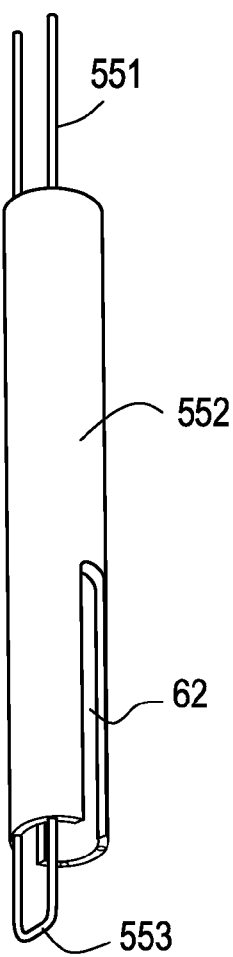
Figure 19C:
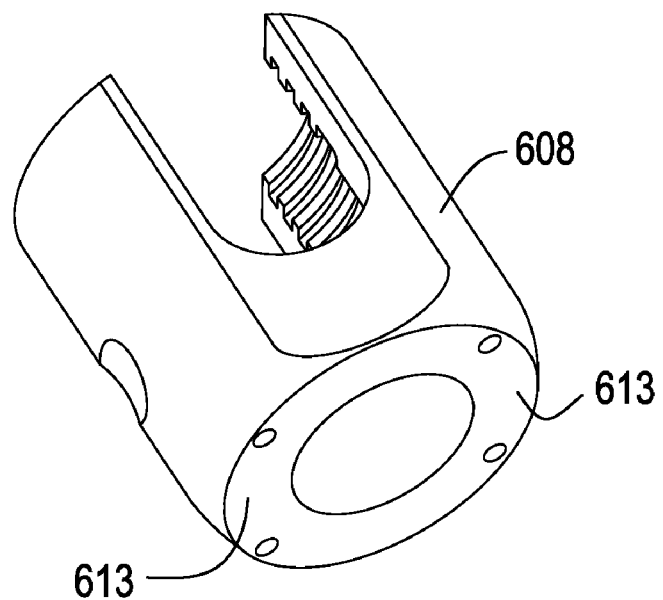
Figure 19D:
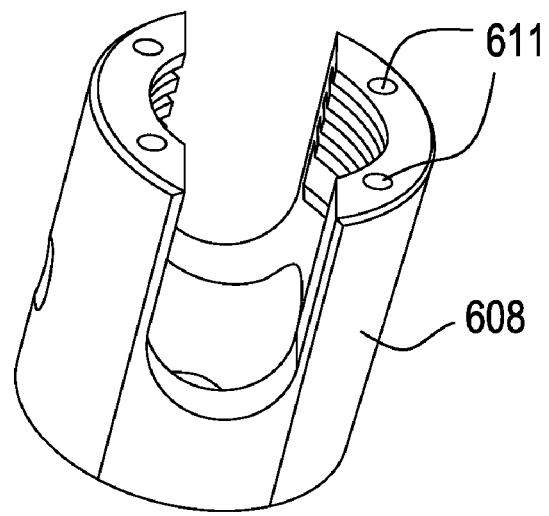
Figure 20A:
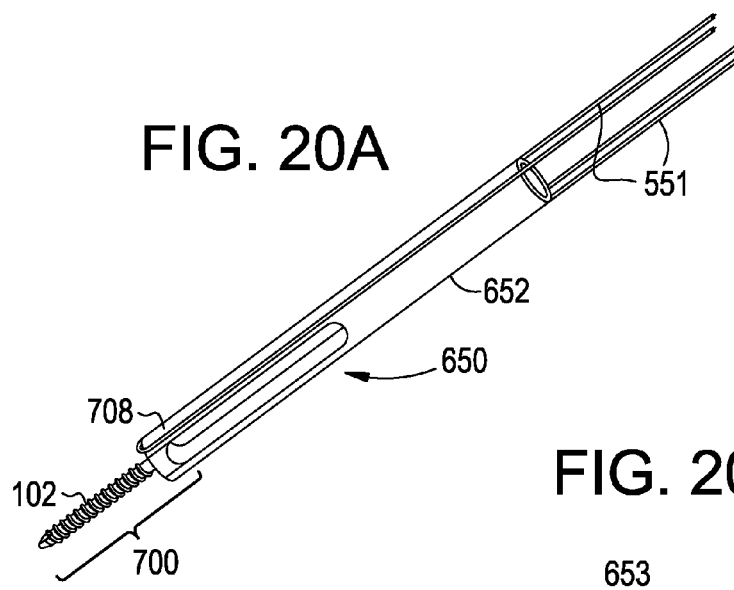
FIGS. 20A-20D are perspective views of an alternative embodiment of a percutaneous access device and a bone anchor assembly, illustrating the percutaneous access device and the bone anchor assembly interconnected by one or more external wires.
Figure 20B:
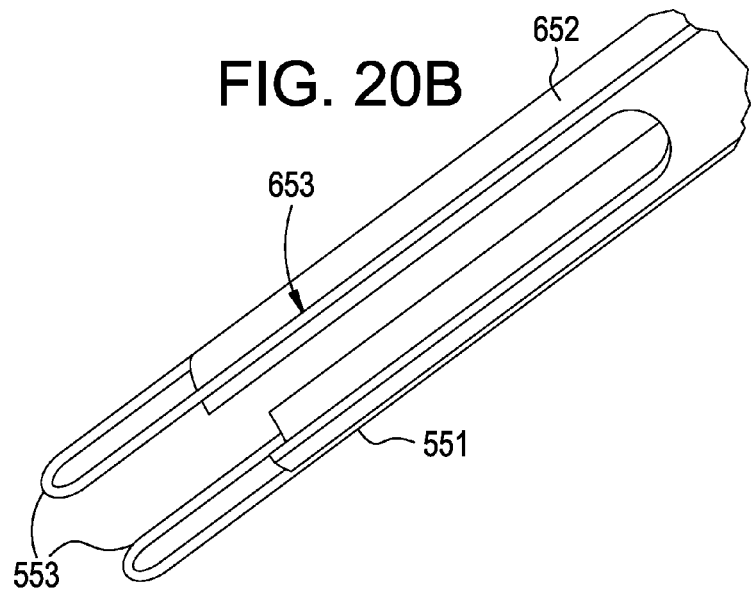
Figure 20C:
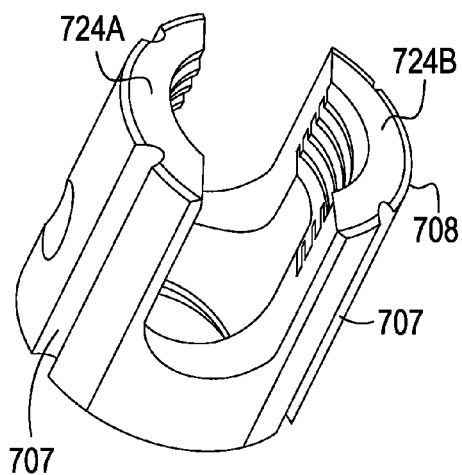
Figure 20D:
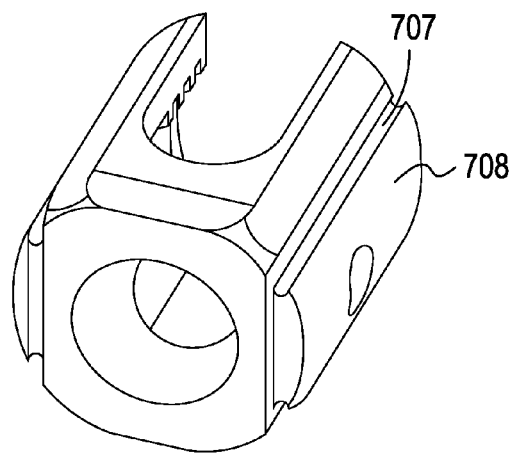

FIGS. 18A and 18B illustrate an alternative embodiment a bone anchor assembly 500, in which the receiving member 508 includes one or more removable, externally threaded tabs 502 that provide a threaded connecting between the percutaneous access device 350 and the bone anchor assembly 500. In the illustrated exemplary embodiment, a pair of proximally extending tabs 502A and 502B extend from the legs 524A and 524B, respectively. Each tab 502, in the illustrated exemplary embodiment, is generally arcuate in shape and includes external threads for engagement with internal threads provided on the percutaneous access device. The tabs 502 may include internal threads 415 to facilitate advancement of a closure mechanism to the bone anchor assembly. Tabs 502 may be sheared off the bone anchor assembly 500 by over tightening of the percutaneous access device 350 or, alternatively, may be removed from the bone anchor assembly 500 after withdrawal of the percutaneous access device 350 by a suitable instrument.

FIGS. 19A-19D illustrate an alternative embodiment of a percutaneous access device 550 and a bone anchor assembly 600, in which the percutaneous access device 500 and the bone anchor assembly 600 are releasably interconnected by one or more internal wires 551. In the illustrated exemplary embodiment, for example, a pair of wires 551, extend axially through opposing side walls of the outer tube 552. Each wire extends through parallel axial holes provided in the side walls of the outer tube 552. Each wire 551 may form a loop 553 that can engage the receiving member 608 of the bone anchor assembly. The wires may be formed of any suitable biocompatible material including, for example a metal, such as a stainless, or a polymer. The receiving member 608, in the exemplary embodiment, includes two pairs of axially extending holes 611 for receiving wires 551. Each pair of holes 611 may terminate in a groove 613 oriented perpendicular to the holes 611. The number of wires and holes provided in the outer tube and the receiving member may be varied depending on the application. Each wire 551 may be tensioned to couple the percutaneous access device 550 to the bone anchor assembly. The wires 551 may be tensioned by, for example, retracting the wires 551 distally. Releasing the tension on the wires 551 by, for example, cutting the wires 551 or advancing the wires 551 proximally, can release the percutaneous access device 550 from the bone anchor assembly 600. In the illustrated exemplary embodiment, the percutaneous access device 550 includes a single tube, outer tube 552; an inner tube may be provided but is not necessary.

FIGS. 20A-20D illustrates an alternative embodiment of a percutaneous access device 650 and a bone anchor assembly 700 in which the percutaneous access device 650 and the bone anchor assembly 700 are releasably interconnected by one or more externally positioned wires 551. The illustrated exemplary embodiment, wires 551 extend axially along the exterior surface of the outer tube 652 of the percutaneous access device 650 and extend axially along the exterior surface of the receiving member 708 of the bone anchor assembly 700. The outer tube 652 may include one or more axially oriented grooves 653 in which the wires 551 may be seated. Likewise, the receiving member 708 may include one or more grooves 707 in which the wires 651 may be seated. The number of wires and/or grooves may be varied depending upon the particular application. In the illustrated embodiment, for example, a pair of parallel grooves 653 are provided in opposing sidewalls of the outer tube 652 and a pair of parallel of grooves 707 are provided in the opposing legs 724A, 724B of the receiving member 708. Each wire 551 may be tensioned to couple the percutaneous access device 650 to the bone anchor assembly 700. The wires 551 may be tensioned by, for example, retracting the wires 551 distally. Releasing the tension on the wires 551 by, for example, cutting the wires 551 or advancing the wires 551 proximally, can release the percutaneous access device 650 from the bone anchor assembly 700. In the illustrated exemplary embodiment, the percutaneous access device 650 includes a single tube, outer tube 652; an inner tube may be provided but is not necessary.

Figure 21:
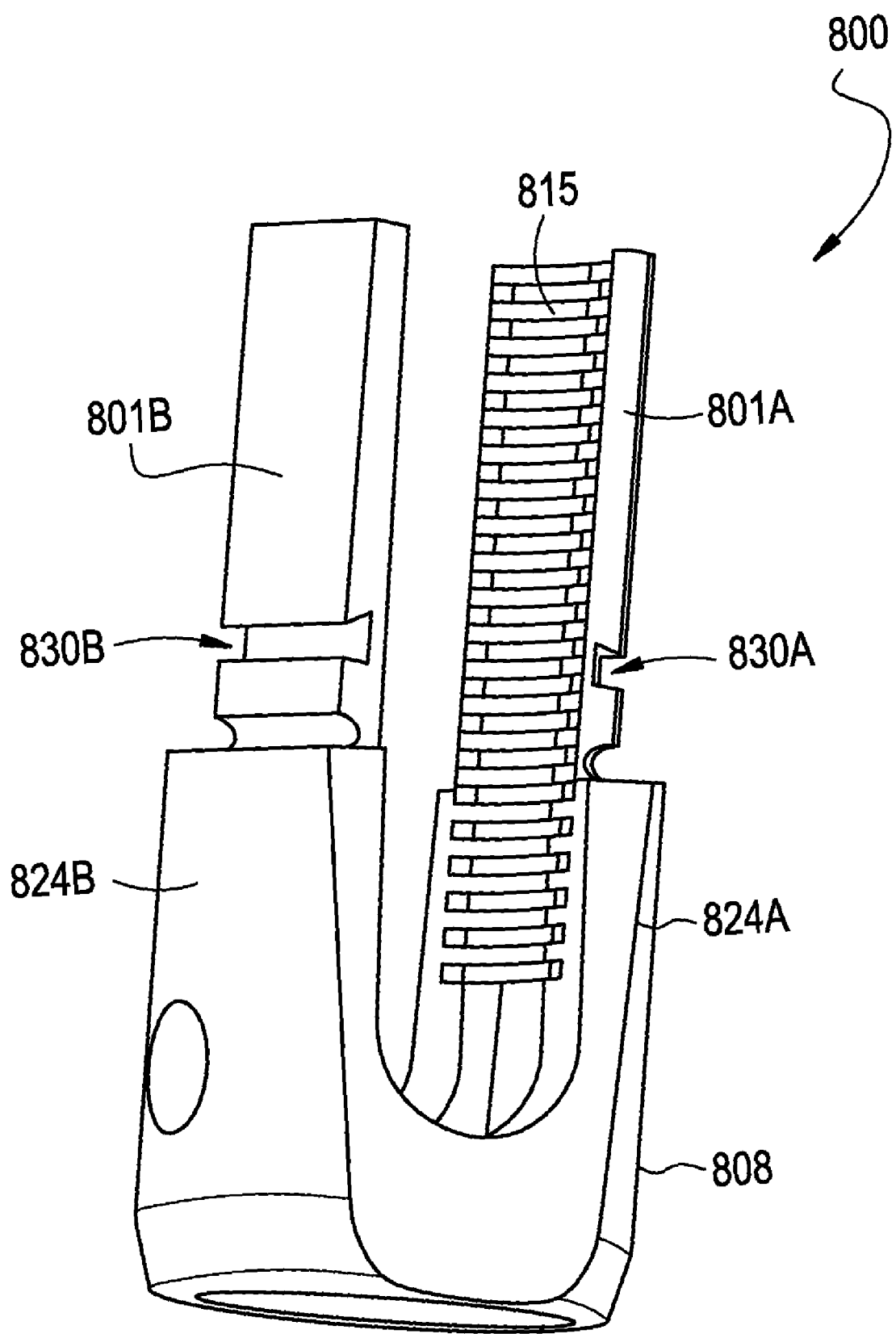
FIG. 21 is a perspective view of an alternative embodiment of a bone anchor assembly having a plurality of removable tabs for releasable engagement with an instrument such as a percutaneous access device.

FIG. 21 illustrates an alternative embodiment of a bone anchor assembly 800 having one or more removable tabs 801 for releasable engagement with an instrument such as an embodiment of a percutaneous access device described above. In the illustrated exemplary embodiment, a pair of opposing tabs 801A, 801B extend proximally from the proximal end of the receiving member 808 of the bone anchor assembly 800. Each tab 801A, 801B, in the illustrated exemplary embodiment, is generally arcuate in shape and are positioned proximal to and extend from a respective leg 824A, 824B of the receiving member 808. The size, shape, and number of tabs 801 may be varied without departing from the scope of the present invention. The tabs 801 may include a mechanism for facilitating releasable engagement by an instrument. For example, the tabs may be provided with external threads, as in the case of the embodiment illustrated in FIGS. 17A, 17B described above, or may include one or more grooves. In the illustrated exemplary embodiment, each tab 801A, 801B includes one or more arcuate grooves 830A, 830B that may be analogous in construction to the grooves 130A, 130B described above. The tabs 801 may include internal threads 815 to facilitate advancement of a closure mechanism to the bone anchor assembly. Tabs 801 may be sheared off the bone anchor assembly 800 by the percutaneous access device or instrument or, alternatively, may be removed from the bone anchor assembly 800 after withdrawal of the percutaneous access device or instrument using a suitable instrument.

Figure 22A:
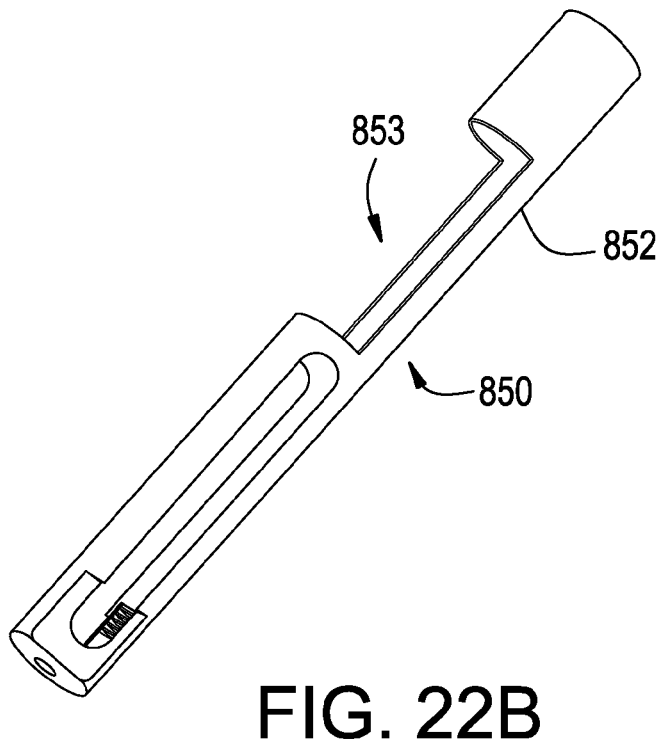
FIGS. 22A-22B are perspective views of an exemplary embodiment of a percutaneous access device, illustrating axial cut-outs provided in the outer tube of the percutaneous access device.
Figure 22B:
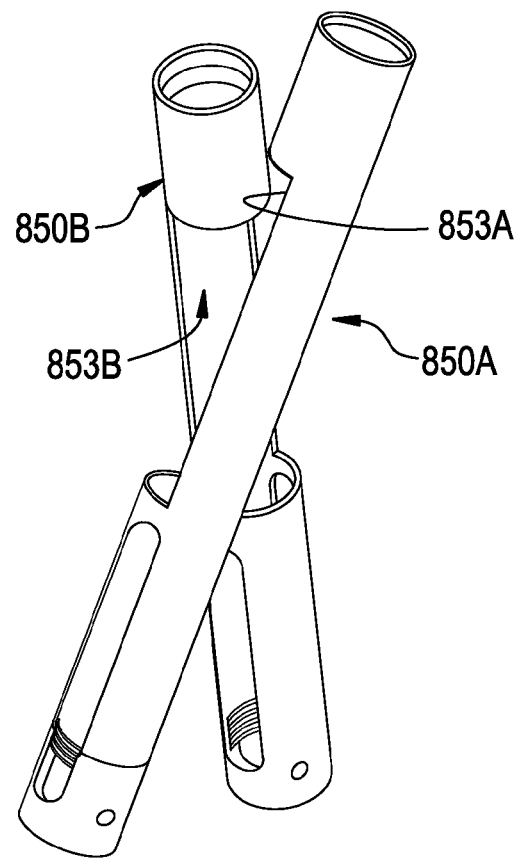

FIGS. 22A-22B illustrates an exemplary embodiment of a percutaneous access device 850 having one or more axially extending cut-outs 853 provided in the outer tube 852 of the percutaneous access device. As illustrated in FIG. 22B, an axially extending cut-out 853 may facilitate the use of multiple percutaneous access devices by minimizing interference between the devices. For example, in certain spinal applications, bone anchors placed on adjacent vertebrae may be closely spaced and/or angled in a manner that may cause interference between instruments, such as a percutaneous access device disclosed herein, used simultaneously with the adjacent bone anchors. By providing axial cut-outs 853, two or more percutaneous access devices 850A, 850B may be employed on adjacent bone anchors, or closely positioned anchors, by aligning the cut-outs 853A, 853B. The length and depth of a cut-out 852 may be varied depending on the application. One or more cut-outs may be provided on any of the exemplary embodiments of the percutaneous access device described herein or with other instruments used with bone anchors, e.g., drills, drivers, cannulas, approximators, and the like. In embodiments including an inner tube or additional tubes, the additional tubes may also be provided with cut-outs 853.

Figure 23A:
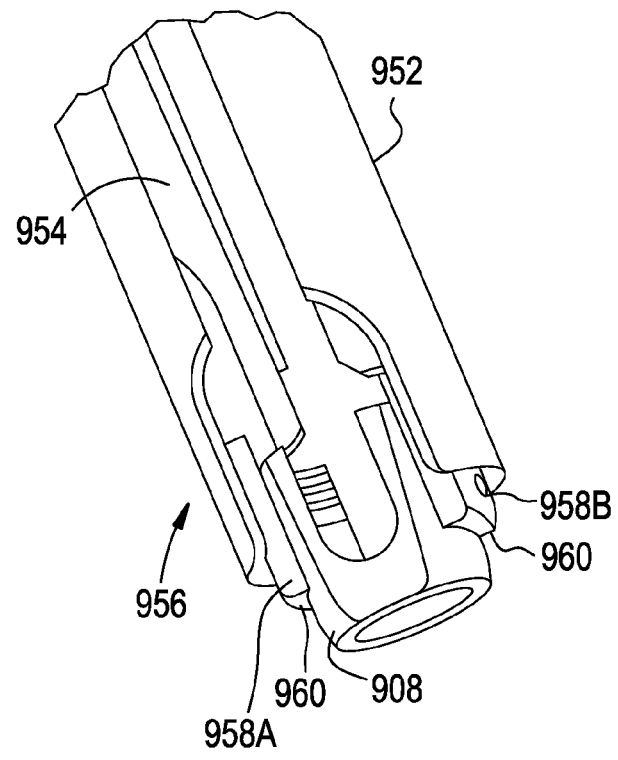
FIGS. 23A-23B are perspective views of an alternative embodiment of a percutaneous access device and a bone anchor assembly, illustrating flexible tabs provided on the distal end of the percutaneous access device for releasable engagement with the bone anchor assembly.
Figure 23B:
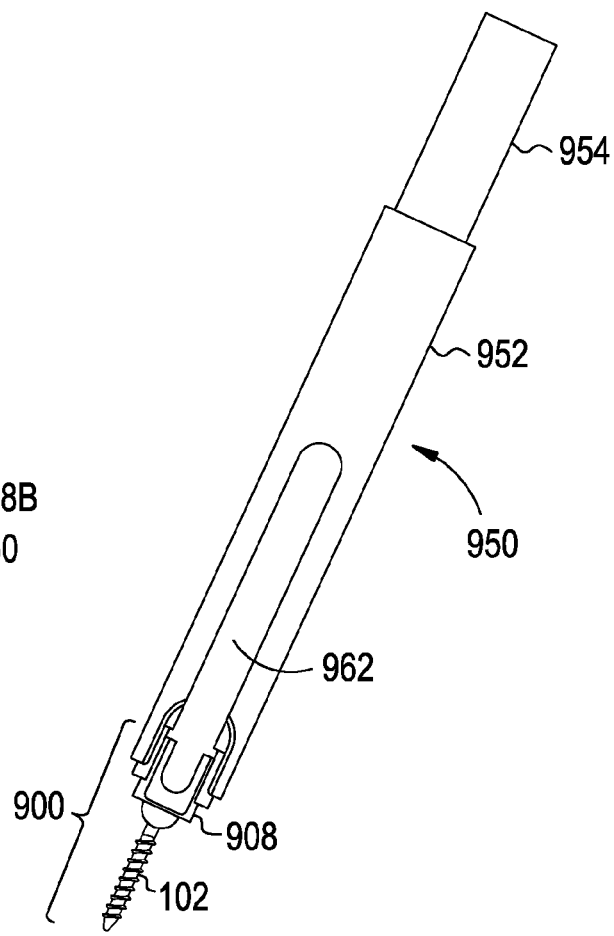

FIGS. 23A-23B illustrates an alternative embodiment of a percutaneous access device 950 and a bone anchor assembly 900 in which the distal end 956 of the inner tube 954 of the percutaneous access device 950 includes one or more flexible bone anchor engaging tabs 958 for releasable engagement with the receiving member 908 of bone anchor assembly 900. In the exemplary embodiment, a pair of opposing tabs 958A, 958B extend distally from the distal end 956 of the inner tube 954. Each tab 958, in the illustrated exemplary embodiment, is connected at a proximal end to the inner tube 954 and has a free distal end 960. One or both of the tabs 958 can flex from a first position, in which the tab 958 is oriented approximately axially, e.g., parallel to the longitudinal axis of the inner tube 954, to a second position, in which the tab 958 is generally oriented at angle to the longitudinal axis of the inner tube 954. In the exemplary embodiment, for example, each tab 958A, 958B may flexed radially outward, e.g., away from each other, from a first position, in which the tabs 958A, 958B are approximately parallel, to a second, flexed positioned, in which the tabs 958A, 958B are oriented at an angle to one another. The tabs 958 may be biased to the first position. For example, the tabs 958A, 958B may be biased to the first, parallel position, such that the tabs 958A, 958B may provide a radially compressive force on the receiving member 908 to releasably engage the receiving member 908. One or more of the tabs 958 may be provided with a projection or the like for engaging a hole, groove, etc, that may be provided in the exterior surface of the receiving member 908. Although the exemplary embodiment includes two tabs 958A, 958B, any number (one or more) tabs 958 may be provided.

The percutaneous access device 950 may include an outer tube 952 that may be advanced about the tabs 958 when the tabs 958 releasably engage the receiving member 908. For example, in the illustrated exemplary embodiment, the outer tube 952 may be advanced distally about the tabs 958A, 958B when the tabs are in the second, flexed position, to inhibit separation of the tabs 958A, 958B and/or provide a radially compressive force on the tabs.

Non-limiting examples of applications of the bone fixation plates described herein include long bone fracture fixation/stabilization, small bone stabilization, lumbar spine as well as thoracic stabilization/fusion, cervical spine compression/fixation, and skull fracture/reconstruction plating.

While the percutaneous access systems and bone anchor assemblies of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

The invention claimed is:

1. In the combination of a bone attachment structure having a receiver and a guide tool having receiver attachment structure at a lower end thereof that is operably mateable with the receiver, the improvement comprising:
   a) the receiver having an aperture and a recess communicating with the aperture; and
   b) the guide tool including a inner tube having a proximal end, a distal end and a lumen extending from the proximal end to the distal end, the inner tube having a first slot formed therein, the first slot opening at the distal end and extending a first slot length toward the proximal end of the inner tube, the guide tool including an outer tube coaxially disposed about the inner tube, the outer tube having a proximal end, a distal end and a lumen extending from the proximal end to the distal end, the outer tube having a second slot formed therein, the second slot opening at the distal end and extending a second slot length toward the proximal end of the outer tube, the distal end of the outer tube having an inner projection, the projection having mating structure receivable in the recess for operably resisting radial splaying and separation of the tool from the receiver when joined together.

2. In the combination of a bone screw having a head and a manipulation tool having attachment structure at a lower end thereof that is operably mateable with the bone screw head; the improvement comprising:
   a) the bone screw head having a top, a bottom, and a circumferentially extending undercut first surface facing downwardly toward said bottom;
   b) the manipulation tool including a inner tube having a proximal end, a distal end and a lumen extending from the proximal end to the distal end, the inner tube having a first slot formed therein, the first slot opening at the distal end and extending a first slot length toward the proximal end of the inner tube, the manipulation tool including an outer tube coaxially disposed about the inner tube, the outer tube having a proximal end, a distal end and a lumen extending from the proximal end to the distal end, the outer tube having a second slot formed therein, the second slot opening at the distal end and extending a second slot length toward the proximal end of the outer tube, the distal end of the outer tube having a projection with a circumferentially extending second surface; and
   c) the first and second surfaces being sized, shaped and positioned to provide for operable mating overlapping alignment of the manipulation tool relative to the bone screw head.

3. The improvement of claim 2 wherein:
   a) the undercut first surface includes a recess and the projection includes extending second surface mating structure that overlaps with the undercut surface in the recess so as to operably resist splaying and separation of the manipulation tool from the receiver when joined together.

4. A spinal system comprising:
   a bone anchor assembly having a bone screw and a receiver member coupled to the bone screw for receiving a spinal fixation element, the receiver member having a proximal end, a distal end, a bore extending from the proximal end to the distal end, and a recess intersecting the bore for receiving the spinal fixation element, the bore defining a bore axis, the proximal end of the receiver member having a generally U-shaped cross-section defined by two spaced apart legs separated by the recess, each leg having a free proximal end including an arcuate groove on an exterior surface thereof, each arcuate groove having a proximal surface, a distal surface, and an interconnecting surface, the proximal surface being angled distally at a non-zero angle relative to a plane orthogonal to the bore axis;
   an instrument having a tubular body, the tubular body having a proximal end, a distal end and a lumen extending from the proximal end to the distal end, the instrument including an inner tube, the tubular body disposed about at least a portion of the inner tube, the tubular body having a pair of opposed tabs separated by a pair of opposed slots, the slots opening at the distal end and extending a slot length toward the proximal end of the tubular body, each tab including an inward projection at a distal end of the tab, each projection being sized and shaped to fit within one of the arcuate grooves of the receiver member and thereby releasable connect the instrument to the bone anchor assembly.

5. The system of claim 4, wherein the proximal surface of each arcuate groove is angled distally at a non-zero angle relative to a plane orthogonal to the bore axis.

6. The system of claim 4, wherein each inward projection of the tabs includes a proximal surface oriented at an angle approximately equal to the angle of the proximal surface of the corresponding arcuate groove.

7. The system of claim 4, wherein the inner tube includes a pair of opposed tabs separated by a pair of opposed slots, the slots opening at a distal end of the inner tube and extending a slot length toward a proximal end of the inner tube.

8. The system of claim 4, wherein the inner tube is adjustable relative to the tubular body along a longitudinal axis of the tubular body.

* * * * *